United States Patent
Ramachandran et al.

(10) Patent No.: US 12,281,021 B2
(45) Date of Patent: Apr. 22, 2025

(54) SYSTEM AND METHOD FOR MAKING BORON OXIDE NANOPARTICLES

(71) Applicant: The Regents of the University of California, Oakland, CA (US)

(72) Inventors: Roshini Ramachandran, West Hollywood, CA (US); Jessica K. Logan, Los Angeles, CA (US); Alexander M. Spokoyny, Los Angeles, CA (US)

(73) Assignee: The Regents of the University of California, Oakland, CA (US)

( * ) Notice: Subject to any disclaimer, the term of this patent is extended or adjusted under 35 U.S.C. 154(b) by 1095 days.

(21) Appl. No.: 15/734,106

(22) PCT Filed: May 31, 2019

(86) PCT No.: PCT/US2019/034817
§ 371 (c)(1),
(2) Date: Dec. 1, 2020

(87) PCT Pub. No.: WO2019/232312
PCT Pub. Date: Dec. 5, 2019

(65) Prior Publication Data
US 2021/0214235 A1    Jul. 15, 2021

Related U.S. Application Data

(60) Provisional application No. 62/679,069, filed on Jun. 1, 2018.

(51) Int. Cl.
C01B 35/10  (2006.01)
B82Y 30/00  (2011.01)
B82Y 40/00  (2011.01)

(52) U.S. Cl.
CPC ........... *C01B 35/1027* (2013.01); *B82Y 30/00* (2013.01); *B82Y 40/00* (2013.01); *C01P 2004/32* (2013.01); *C01P 2004/64* (2013.01)

(58) Field of Classification Search
CPC ..... C01B 35/1027; B82Y 30/00; B82Y 40/00; C01P 2004/32; C01P 2004/64; A61K 41/0095
See application file for complete search history.

(56) References Cited

U.S. PATENT DOCUMENTS

| | | | |
|---|---|---|---|
| 4,342,345 A * | 8/1982 | Nadin ................ | B65G 69/0458 239/666 |
| 2008/0224104 A1 * | 9/2008 | Zaban .................... | B82Y 30/00 252/521.2 |

(Continued)

FOREIGN PATENT DOCUMENTS

| CN | 1438176 A | 8/2003 |
|---|---|---|
| WO | 1999062079 A1 | 12/1999 |
| WO | 2010124245 A2 | 10/2010 |

OTHER PUBLICATIONS

Van Devener et al. "Air-stable, unoxidized, hydrocarbon-dispersible boron nanoparticles" J. Mater. Res., Nov. 2009 vol. 24, No. 11, p. 3462-3464 (Year: 2009).*

(Continued)

*Primary Examiner* — Wayne A Langel
*Assistant Examiner* — Syed T Iqbal
(74) *Attorney, Agent, or Firm* — Quarles & Brady LLP

(57) ABSTRACT

A method of making boron oxide nanoparticles. The method can comprise sonochemically treating a composition comprising a boron oxide to form boron oxide nanoparticles. The method allows for the formation of these nanoparticles from non-toxic, inexpensive reagents and ambient reaction con- (Continued)

ditions. Additionally, the nanoparticles produced by the teachings described herein can be easily surface functionalized.

10 Claims, 21 Drawing Sheets

(56) References Cited

U.S. PATENT DOCUMENTS

2010/0069229 A1   3/2010   Yang
2013/0004412 A1   1/2013   Iyer
2014/0322823 A1  10/2014   Alocilja

OTHER PUBLICATIONS

Thanh et al. "Functionalisation of nanoparticles for biomedical applications" Nano Today (2010) 5, 213-230 (Year: 2010).*
Bloemen et al. "Improved functionalization of oleic acid-coated iron oxide nanoparticles for biomedical applications", J Nanopart Res (2012) 14:1100, p. 1-10 (Year: 2012).*
Alizadeh et al. "Production of Nanosized Boron Oxide Powder by High-Energy Ball Milling" Synthesis and Reactivity in Inorganic, Metal-Organic, and Nano-Metal Chemistry, 45: 11-14, 2015 (Year: 2015).*
Ramachandran et al. "Sonochemical Synthesis of Small Boron oxide Nanoparticles" Inorg. Chem. Jun. 2018, 57, 8037-8041 (Year: 2018).*
Achilli, C. et al. Biocompatibility of Functionalized Boron Phosphate (BPO4) Nanoparticles for Boron Neutron Capture Therapy (BNCT) Application. Nanomedicine 2014, 10, 589-597.
Al-Rashdi, B.; et al. Copper Removal from Aqueous Solutions Using Nano-scale Diboron Trioxide/Titanium Dioxide (B2O3/TiO2) Adsorbent. Chem. Eng. J. 2012, 183, 294-302.
Ay, A. N. et al. Carborane-layered Double Hydroxide Nanohybrids for Potential Targeted- and Magnetically Targeted-BNCT Applications. Dalton Trans. 2017, 46, 3303-3310.
Balci, S. et al. Boron Oxide Production Kinetics Using Boric Acid as Raw Material. Ind. Eng. Chem. Res. 2012, 51, 11091-11096.
Boroica, L.; et al. FTIR Spectra of Glasses from BaO—B2O3—TiO2 System. J. Optoelectron. Adv. M. 2008, 10, 3217-3220.
Buc, D.; et al. Analysis of Magnetron Sputtered Boron Oxide Films. Thin Solid Films. 2007, 515, 8723-8727.
Chang, L.C. et al. Effect of B2O3 Nano-Coating on the Sintering Behaviors and Electrical Microwave Properties of Ba(Nd2—xSmx)Ti4O12 Ceramics. J. Electroceramics. 2004, 13, 829-837.
Chen, W.; et al. Selective Boron Drug Delivery to Brain Tumors for Boron Neutron Capture Therapy. Adv. Drug Deliv. Rev. 1997, 26, 231-247.
Ciofani, G. et al. Folate Functionalized Boron Nitride Nanotubes and their Selective Uptake by Glioblastoma Multiforme Cells: Implications for their Use as Boron Carriers in Clinical Boron Neutron Capture Therapy. Nanoscale Res. Lett. 2009, 4, 113-121.
Frey, N.A. et al. Magnetic Nanoparticles: Synthesis, Functionalization, and Applications in Bioimaging and Magnetic Energy Storage. Chem. Soc. Rev. 2009, 38, 2532-2542.
Fullerton, S.K.; et al. A Molecular Dynamics Study of the Structural Dependence of Boron Oxide Nanoparticles on Shape. Nano Lett. 2005, 5, 363-368.
Hanst, P.L.; et al. Infrared Spectrum and Molecular Structure of B2O3. J. Chem. Phys. 1965, 42, 1097-1104.
Harada, T.; et al. Effect of B2O3 Addition on the Thermal Stability of Barium Phosphate Glasses for Optical Fiber Devices. J. Am. Ceram. Soc. 2004, 87, 408-411.
Hawthorne, F. M. The Role of Chemistry in the Development of Boron Neutron Capture Therapy of Cancer. Angew. Chem. Int. Ed. Engl. 1993, 32, 950-984.
Hosmane, N.S. et al. Nano and Dendritic Structured Carboranes and Metallacarboranes: From Materials to Cancer Therapy. J. Organomet. Chem. 2009, 694, 1690-1697.

International Searching Authority. International Search Report and Written Opinion for application PCT/US2019/034817. Mailed on Sep. 27, 2019. 12 pages.
Jaeger, C.; et al. Easy: A Simple Tool for Simultaneously Removing Background, Deadtime and Acoustic Ringing in Quantitative NMR Spectroscopy—Part I: Basic Principle and Applications. Solid State Nucl. Mag. 2014, 57, 22-28.
Joni, I.M. et al. Surface Functionalization for Dispersing and Stabilizing Hexagonal Boron Nitride Nanoparticle by Bead Milling. Colloids Surf. A 2011, 388, 49-58.
Jung, D., et al. "A molecular cross-linking approach for hybrid metal oxides." Nature materials 17.4 (2018): 341-348.
Kalfa, O.M.; et al. Synthesis of nano B2O3/TiO2 Composite Material as a New Solid Phase Extractor and its Application to Preconcentration and Separation of Cadmium. J. Hazard. Mater. 2009, 166, 455 461.
Kim, J. et al. Neutron Shielding Characteristics of Nano-B2O3 Dispersed Poly Vinyl Alcohol. In Transactions of the Korean Nuclear Society Spring Meeting. May 29, 2008. 29-30.
Kolmakov, A. et al. Chemical Sensing and Catalysis by One-dimensional Metal oxide Nanostructures. Annu. Rev. Mater. Res. 2004, 34, 151-180.
Kroeker, S; et al. Three-coordinated Boron-11 Chemical Shifts in Borates. Inorg. Chem. 2001, 40, 6239-6246.
Kuthala, N.; et al. Engineering Novel Targeted Boron-10-Enriched Theranostic Nanomedicine to Combat against Murine Brain Tumors via MR Imaging-Guided Boron Neutron Capture Therapy. Adv. Mater. 2017, 29, 1700850.
Aurent, S. et al. Magnetic Iron Oxide Nanoparticles: Synthesis, Stabilization, Vectorization, Physicochemical Characterizations, and Biological Applications. Chem. Rev. 2008, 108, 2064-2110.
Longmire, M. et al. Clearance Properties of Nano-sized Particles and Molecules as Imaging Agents: Considerations and Caveats. Nanomedicine 2008, 3, 703-717.
Mahdavi, M. et al. Synthesis, Surface Modification and Characterisation of Biocompatible Magnetic Iron Oxide Nanoparticles for Biomedical Applications. Molecules 2013, 18, 7533-7548.
Mandal, S. et al. Design, Development and Characterization of Multi-functionalized Gold Nanoparticles for Biodetection and Targeted Boron Delivery in BNCT Applications. Appl. Radiat. Isot. 2011, 69, 1692-1697.
Moon, O.M. et al. Temperature Effect on Structural Properties of Boron Oxide Thin Films Deposited by MOCVD Method. Thin Solid Films 2004, 464-465, 164-169.
Mortensen, M.W.; et al. Functionalization and Cellular Uptake of Boron Carbide Nanoparticles. The First Step Toward T Cell-guided Boron Neutron Capture Therapy. Bioconjug. Chem. 2006, 17, 284-290.
Mortensen, M.W.; et al. Preparation and Characterization of Boron Carbide Nanoparticles for Use as a Novel Agent in T Cell-guided Boron Neutron Capture Therapy. Appl. Radiat. Isot. 2006, 64, 315-324.
Oleshkevich, E.; et al. Merging Icosahedral Boron Clusters and Magnetic Nanoparticles: Aiming toward Multifunctional Nanohybrid Materials. Inorg. Chem. 2018, 57, 462-470.
Perez, J.P.L. et al. Functionalization and Passivation of Boron Nanoparticles with a Hypergolic Ionic Liquid. J. Propul. Power 2013, 29, 489-495.
Perez, J.P.L. Preparation and Characterization of Surface Functionalized Boron Nanoparticles for Fuel and Propellant Applications. Ph.D. Thesis. The University of Utah, Salt Lake City, UT, 2013.
Ramachandran, R. et al. Nanostructuring of Strontium Hexaboride via Lithiation. Inorg. Chem. 2018, 57, 4-7.
Ramachandran, R., et al. "Sonochemical synthesis of small boron oxide nanoparticles." Inorganic chemistry 57.14 (Jun. 25, 2018): 8037-8041.
Rhim, S.M.; et al. Effects of B2O3 Addition on the Dielectric and Ferroelectric Properties of Ba0.7Sr0.3TiO3 ceramics. J. Am. Ceram. Soc. 2000, 83, 1145-1148.
Sayyed, M.I.; et al. Variation of Energy Absorption and Exposure Buildup Factors with Incident Photon Energy and Penetration Depth for Boro-tellurite (B2O3—TeO2) Glasses. Radiat. Phys. Chem. 2017, 130, 335-342.

(56) References Cited

OTHER PUBLICATIONS

Schmid, G.; et al. Effect of Free Fatty Acids and Phospholipids on Growth of and Product Formation by Recombinant Baby Hamster Kidney (rBHK) and Chinese Hamster Ovary (rCHO) Cells in Culture. J. Biotechnol. 1991, 17, 155-167.

Singh, H.; et al. ZnO—PbO—B2O3 Glasses as Gamma-ray Shielding Materials. Nucl. Instr. Meth. Phys. Res. B 2003, 207, 257-262.

Thanh, N.T.K. et al. Functionalisation of Nanoparticles for Biomedical Applications. Nano Today 2010, 5, 213-230.

Van Devener, B. et al. Air-stable, Unoxidized, Hydrocarbon-dispersible Boron Nanoparticles. J. Mater. Res. 2009, 24, 3462-3464.

Wang, X. et al. A General Strategy for Nanocrystal Synthesis. Nature 2005, 437, 121-124.

Wilson, D.; et al. XPS Analysis of Oleylamine/Oleic Acid Capped Fe3O4 Nanoparticles as a Function of Temperature. Appl. Surf. Sci. 2014, 303, 6-13.

Yinghuai, Z. et al. Recent Developments in Boron Neutron Capture Therapy (BNCT) Driven by Nanotechnology. Curr. Chem. Biol. 2007, 1, 141-149.

Yinghuai, Z. et al. Substituted Carborane-appended Water-soluble Single-wall Carbon Nanotubes: New Approach to Boron Neutron Capture Therapy Drug Delivery. J. Am. Chem. Soc. 2005, 127, 9875-9880.

Yu, X.; et al. Metal Oxides for Optoelectronic Applications. Nature Mater. 2016, 15, 383-396.

Zhang, L. et al. Oleic Acid Coating on the Monodisperse Magnetite Nanoparticles. Appl. Surf. Sci. 2006, 253, 2611-2617.

Zhi, C.Y.; et al. Boron Nitride Nanotubes: Functionalization and Composites. J. Mater. Chem. 2008, 18, 3900-3908.

Zhu, Y. et al. Boron Drug Delivery via Encapsulated Magnetic Nanocomposites: a New Approach for BNCT in Cancer Treatment. J. Nanomater. 2010, 24-31.

Zhu, Y. et al. Nanostructured Boron Compounds for Cancer Therapy. Pure Appl. Chem. 2017, 90, 653-663.

Nedunchezhian et al., Boron Neutron Capture Therapy—A Literature Review, Journal of Clinical and Diagnostic Research, 2016, 10(12):ZE01-ZE04.

European Patent Office, Extended Search Report, Application No. 19811972.9, May 30, 2022, 16 pages.

Nanoshel (UK) Limited, "Specification Sheet, Degussa TiO2 p. 25 Nanoparticles", 2 pages, date unknown.

\* cited by examiner

SYSTEM AND METHOD FOR MAKING BORON OXIDE NANOPARTICLES

CROSS-REFERENCE TO RELATED APPLICATIONS

This application represents the national stage entry of International Application PCT/US2019/034817, filed May 31, 2019, which is based on, claims priority to, and incorporates herein by reference in its entirety U.S. Ser. No. 62/679,069 filed Jun. 1, 2018, and entitled "System and Method for Making Boron Oxide Nanoparticles."

STATEMENT REGARDING FEDERALLY SPONSORED RESEARCH

This invention was made with government support under GM124746 awarded by the National Institutes of Health. The government has certain rights in the invention.

BACKGROUND

The present disclosure relates to systems and methods for synthesizing nanoscale particles. More particularly, the present disclosure provides systems and methods for making boron oxide nanoparticles.

Nanoscale architectures of oxide-based materials have been extensively developed due to their diverse applications in the areas ranging from photonics to drug delivery. The properties of nanomaterials can be altered by tuning their morphology, which is beneficial to tailor materials for specific applications. Although efforts at nanostructuring metal and non-metal oxides (e.g., $TiO_2$, $Fe_2O_3$, $SiO_2$, $Al_2O_3$) have garnered much attention over the years, there has been limited research conducted on synthetic methods for producing well-defined nanoscale $B_2O_3$ systems. Bulk $B_2O_3$ is a commonly used component in oxide glasses and ceramics for radiation shielding, optical, and dielectric applications. Unfortunately, processing options for bulk $B_2O_3$ require high temperatures for melting and sintering, as well as specialized equipment. The development of nanoscale $B_2O_3$ would therefore be potentially useful for creating solution-processable coating materials, or for fabricating novel composite materials that contain discrete amounts of $B_2O_3$ nanoparticles. Computational predictions on the structure and morphologies of nano-$B_2O_3$ have been theoretically explored, however, experimental endeavors to synthesize nanoscale boron oxide remain largely unsuccessful. Prior attempts at nanostructuring boron oxide-based materials have primarily used ball-milling, which presents limitations with respect to the size and homogeneity of the nanoproducts formed. Furthermore, due to the moderate solubility of $B_2O_3$ in water, it is not feasible to apply solution-based, bottom-up synthetic routes (co-precipitation, hydrothermal, and aqueous sol-gel) that precipitate out insoluble metal oxides.

Turning to one possible application for $B_2O_3$ nanoparticles, there has been a long-standing history in the development of boron-rich compounds suitable for boron neutron capture therapy (BNCT). This technology is potentially promising for treatment of metastatic tumors (e.g., glyoblastoma carcinoma) and skin cancers. Recently, there has been a revived interest in this approach given the breakthroughs achieved in medical neutron generation that do not rely on nuclear reactors. These developments further drive the need to create boron-rich scaffolds that are non-toxic and amenable to functionalization. To date, boron-based nanomaterials synthesized for potential use in BNCT include boron nanocomposites, boron nitride, boron carbide, and various boronated and boron-functionalized nanostructures. However, their relatively large sizes and morphologies could lead to a lower nanomaterial cellular uptake. Additionally, larger nanomaterials (>50 nm) are known to have difficulty penetrating the blood brain barrier, and show increased accumulation in the body.

Therefore, it would be desirable to have systems and methods for synthesizing nanoscale boron particles without the limitations of size and homogeneity that traditional methods have. Small, uniform boron nanoparticle compositions would have the potential to be immensely beneficial to BNCT as well as other applications.

BRIEF SUMMARY

The present disclosure addresses the aforementioned needs by providing systems and methods that allow for the synthesis of boron oxide nanoparticles using a facile process that can rely on novel top-down sonochemical approach. The described techniques are capable of producing compositions of very small boron oxide nanoparticles that have a high degree of uniformity. Unlike many prior methods, the formation techniques discussed herein require very few intermediary steps, can use readily-available starting materials, and do not require harsh operating conditions.

In one aspect, the present disclosure provides a method of making boron oxide nanoparticles. The method can comprise sonochemically treating a solution comprising a boron oxide to form boron oxide nanoparticles.

In another aspect, the present disclosure provides a composition. The composition can comprise a plurality of boron oxide nanoparticles having an average cross-sectional diameter of less than 5 nanometers with a standard deviation of less than 1 nanometer.

In yet another aspect, the present disclosure provides a composition for use as an agent for neutron capture therapy of cancer. The composition can comprise boron oxide nanoparticles, wherein the boron oxide nanoparticles have an average cross-sectional diameter of less than 50 nanometers and are isotopically labeled with Boron-10.

In still another aspect, the present disclosure provides a system for making boron oxide nanoparticles. The system can comprise a solution comprising boron trioxide and a probe sonicator configured to apply sound energy to the solution to form boron oxide nanoparticles.

In yet another aspect, the present disclosure provides a composition for use as a precursor to an agent for proton beam therapy is provided. The composition may comprise boron oxide nanoparticles, wherein the boron oxide nanoparticles have an average cross-sectional diameter of less than 50 nanometers and are isotopically labeled with Boron-11.

The foregoing and other aspects and advantages of the disclosure will appear from the following description. In the description, reference is made to the accompanying drawings which form a part hereof, and in which there is shown by way of illustration a preferred configuration of the disclosure. Such configuration does not necessarily represent the full scope of the disclosure, however, and reference is made therefore to the claims and herein for interpreting the scope of the disclosure.

BRIEF DESCRIPTION OF DRAWINGS

The invention will be better understood and features, aspects and advantages other than those set forth above will become apparent when consideration is given to the following detailed description thereof. Such detailed description makes reference to the following drawings.

FIG. 2A: SEM image of bulk $B_2O_3$; FIG. 2B: low-magnification TEM image of OA-$B_2O_3$ NPs, inset high-magnification TEM image: FIG. 2C: low-magnification TEM image of CMD-$B_2O_3$ NPs, inset high-magnification TEM image; FIG. 2D: FTIR spectra of bulk $B_2O_3$, OA-$B_2O_3$ NPs and CMD-$B_2O_3$ NPs; FIG. 2E: B 1s and O 1s XPS spectra of bulk $B_2O_3$, OA-$B_2O_3$ NPs and CMD-$B_2O_3$ NPs.

FIG. 4A: TEM image of OA-$^{10}B_2O_3$ NPs, inset SAED with labeled indices for prominent rings; FIG. 4B: HRTEM image of CMD-$^{10}B_2O_3$ NPs; FIG. 4C: flow cytometry of CHO cells incubated with no nanoparticles, OA-$B_2O_3$ NPs, OA-$^{10}B_2O_3$ NPs, CMD-$B_2O_3$ NPs, or CMD-$^{10}B_2O_3$ NPs for 24 hours. Dead cells were characterized as exhibiting fluorescence greater than $10^2$. Error bars represent the standard deviation of three replicate samples.

DETAILED DESCRIPTION

As used herein, the term "nontoxic" carries its general meaning in the art as it relates to mammalian cell health. For example, a "nontoxic" substance may be one that does not directly cause substantial cell death at a specified concentration. More specifically, a "nontoxic" substance may be one that, when provided to Chinese hamster ovary (CHO) cells incubated at conditions comparable to those of the examples experiments herein, results in cell death of less than 1%, 2%, 5%, or 10% after 24 hours, 48 hours, or 1 week for a given concentration.

As used herein, the term "capping agent" may refer to a substance that inhibits nanoparticle overgrowth and aggregation during synthesis and controls the structural characteristics of the resulted nanoparticles in a precise manner. In order to achieve this functionality, a capping agent may cover the surface of nanoparticles, thereby shielding the particles from coagulation or aggregation. Because the effectiveness of capping agents can vary based on nanoparticle composition, the term "capping agent" in the present disclosure may generally refer to a substance that inhibits boron oxide nanoparticle overgrowth.

The novel systems and methods described herein allow for the synthesis of boron oxide nanoparticles using a facile process. The present disclosure allows for the formation of these nanoparticles from non-toxic, inexpensive reagents, and ambient reaction conditions. Typically, stronger conditions such as high temperatures and pH, or the use of strong reducing agents are required to yield uniformly sized nanoparticles. The present disclosure achieves small, uniform nanoparticles without using any of these unfavorable reagents or reaction conditions. Additionally, the nanoparticles produced by the teachings described herein can be easily surface functionalized. An additional noteworthy aspect of the present disclosure is the non-toxicity of the boron oxide nanoparticles to mammals, making them prospective candidates for agents or precursors to agents to be used in boron neutron capture therapy (BNCT).

As will be described, the systems, methods, and compositions of the present disclosure may be configured for use in a variety of applications, including, as a non-limiting example, the creation of $B_2O_3$ nanoparticles to be used in boron neutron capture therapy.

Figure 1:
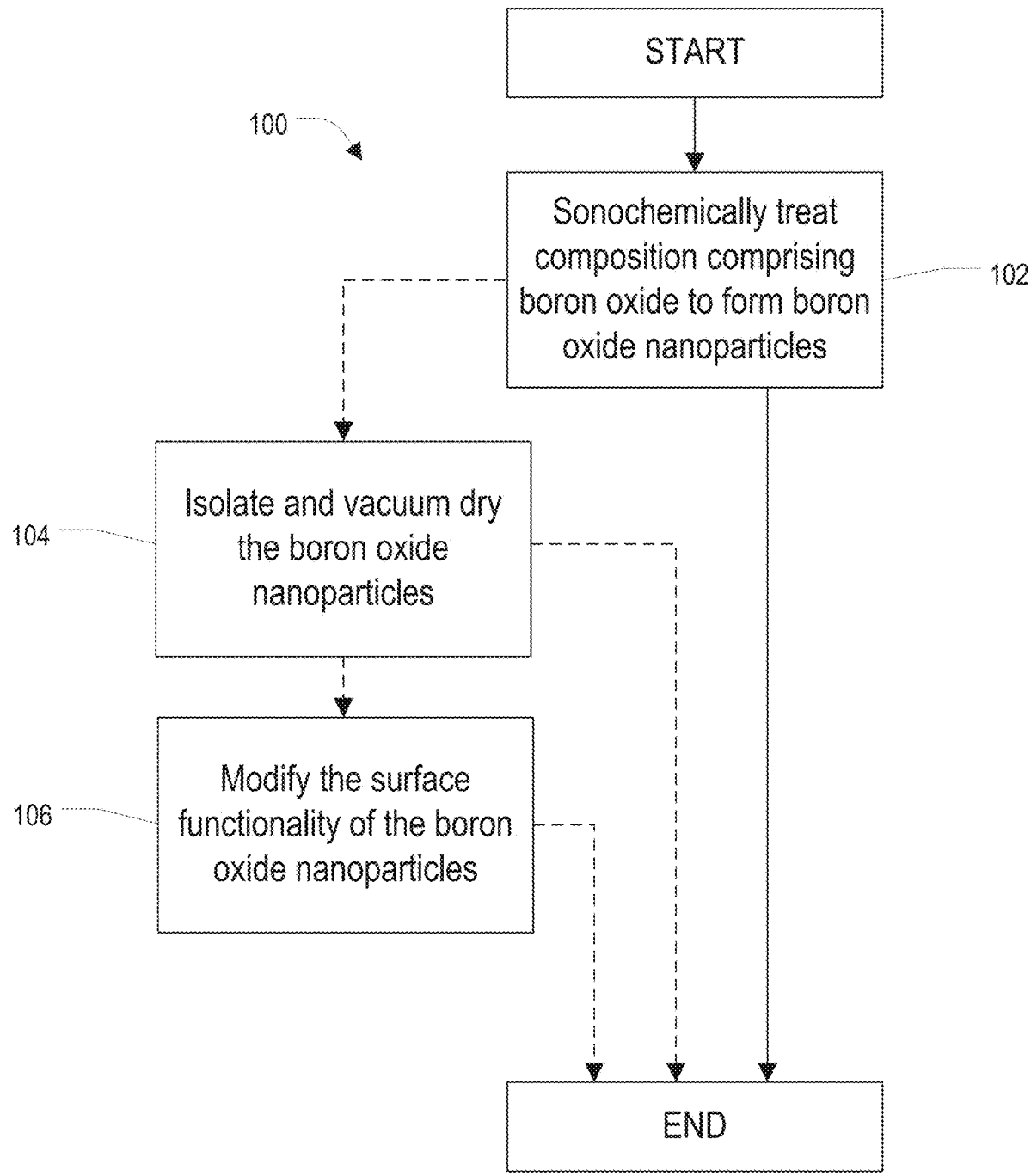
FIG. 1 depicts a process flowchart of a method of making boron oxide nanoparticles, in accordance with one aspect of the present disclosure.

FIG. 1 depicts a process flowchart of a method 100 of making boron oxide nanoparticles. The method comprises a first step 102 of sonochemically treating a composition comprising a boron oxide to form boron oxide nanoparticles. The boron oxide may specifically be boron trioxide. The solution may comprise at least one capping agent. For instance, the solution may contain oleic acid as a capping agent. The capping agent may be in the form of a liquid. The boron oxide may be dissolved or suspended in the liquid prior to the method step of sonication. The method step 102 of sonochemically treating the solution may comprise applying probe sonication to the solution at sufficient energy levels and for a suitable time period to synthesize the boron oxide nanoparticles. For instance, the solution may be probe sonicated for at least 10 minutes, at least 30 minutes, at least 1 hour, between 1 and 5 hours, between 2 and 4 hours, or for about 3 hours. A probe sonicator similar to the QSonica Q125 sonicator may be used to apply the probe sonication at an amplitude of about 50. The solution may be chilled during the sonochemical treatment step using an ice bath or an alternative cooling system.

The method may comprise a second step 104 of isolating and vacuum drying the boron oxide nanoparticles. For instance, the boron oxide nanoparticles and the solution may be centrifuged to remove the supernatant fluid and then vacuum dried using a lyophilizer. Once vacuum dried, the boron oxide nanoparticles may be in the form of a solid powder.

The method may further comprise a third step 106 of modifying the surface functionality of the nanoparticles. For instance, the third step may comprise solubilizing the boron oxide nanoparticles. Solubilizing the boron oxide nanoparticles may include contacting the nanoparticles with a water-soluble capping agent for a sufficient period of time. The water-soluble capping agent may specifically be carboxymethyl-dextran. Once solubilized, the nanoparticles may characterized as being fully soluble in deionized water. This third step may comprise stirring the boron oxide nanoparticles in a solution comprising a water-soluble capping agent. Unlike prior methods for functionalizing boron-based nanostructures which often involve coupling chemical reactions or milling, simple agitation may be sufficient to produce such surface modifications.

In one aspect, a composition comprising a plurality of boron oxide nanoparticles having an average cross-sectional diameter of less than 5 nanometers with a standard deviation of less than 1 nanometer is provided. The boron oxide nanoparticles may comprise boron trioxide. The composition may be soluble in aqueous solutions. The boron oxide nanoparticles may comprise a water soluble capping agent. For instance, the water-soluble capping agent may be carboxymethyl-dextran. The composition may be a composite with the boron oxide nanoparticles being homogenously distributed throughout the composition. For instance, the composition may be a polymer or ceramic with the boron oxide nanoparticles distributed throughout. Alternatively, the composition may be in the form of a film applied to an article. Including an appropriate concentration of the boron oxide nanoparticles in the solution may allow the material to function as a radiation shield.

In another aspect, a composition for use as an agent for neutron capture therapy of cancer is provided. The composition may comprise boron oxide nanoparticles, wherein the boron oxide nanoparticles have an average cross-sectional diameter of less than 50 nanometers and are isotopically labeled with Boron-10. The small size of the boron oxide nanoparticles may allow for improved targeting of cancerous tumors by, for example, allowing for increased nanomaterial cellular uptake. The composition may be a precursor to an agent for boron neutron capture therapy. The boron oxide nanoparticles of the composition may have a substantially spherical shape. The boron oxide nanoparticles may comprise boron trioxide. The boron oxide nanoparticles may be in the form of a dry powder. The composition may be soluble in aqueous solutions. The composition may be non-toxic to mammalian cells at concentrations of less than 1 mM. The composition may be non-toxic to mammalian cells at concentrations of less than 1.7 mM.

In yet another aspect, a composition for use as a precursor to an agent for proton beam therapy is provided. The composition may comprise boron oxide nanoparticles, wherein the boron oxide nanoparticles have an average cross-sectional diameter of less than 50 nanometers and are isotopically labeled with Boron-11. The small size of the boron oxide nanoparticles may allow for improved targeting of cancerous tumors by, for example, allowing for increased nanomaterial cellular uptake. The composition may be a precursor to an agent for boron neutron capture therapy. The boron oxide nanoparticles of the composition may have a substantially spherical shape. The boron oxide nanoparticles may comprise boron trioxide. The boron oxide nanoparticles may be in the form of a dry powder. The composition may be soluble in aqueous solutions. The composition may be non-toxic to mammalian cells at concentrations of less than 1 mM. The composition may be non-toxic to mammalian cells at concentrations of less than 1.7 mM. The unique composition of the nanoparticles may lead to a significant enhancement of the efficacy of various proton-beam therapy treatments.

Figure 20:
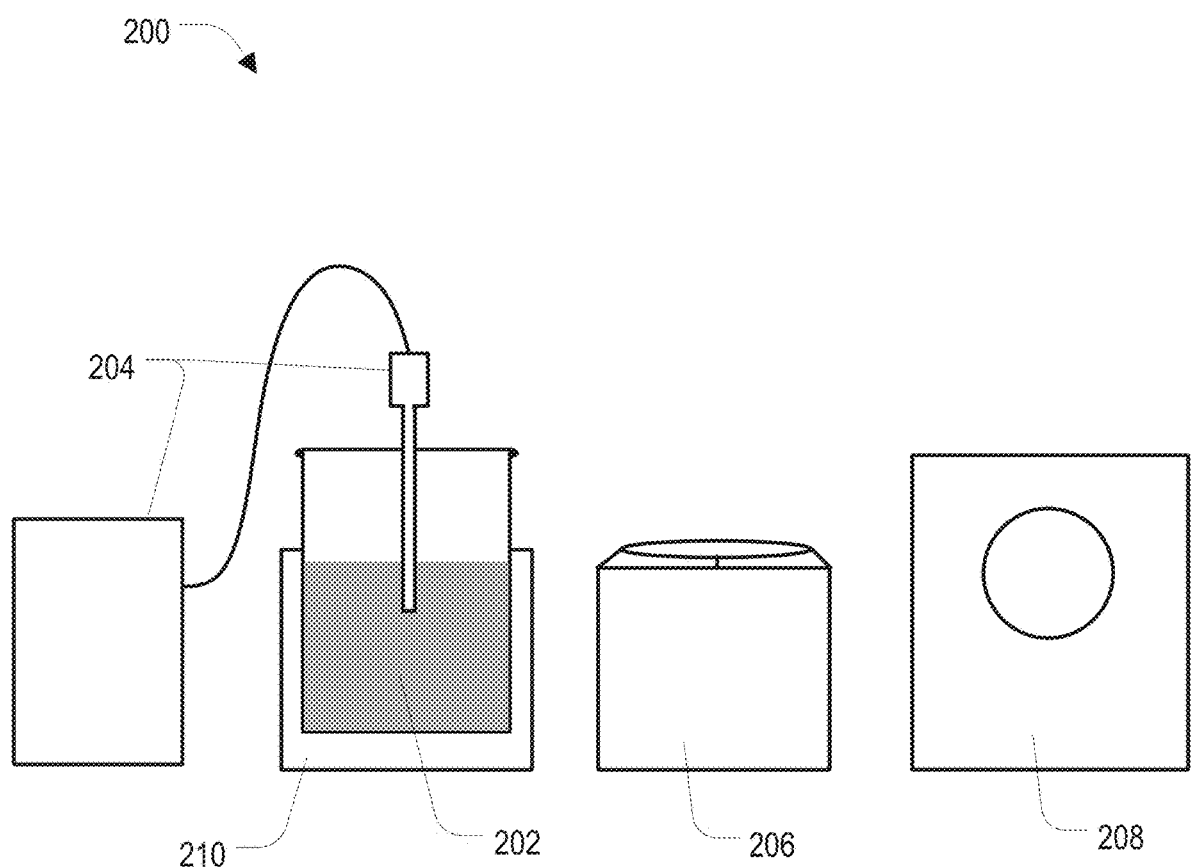
FIG. 20 depicts a schematic illustration of a system for making boron oxide nanoparticles, in accordance with one aspect of the present disclosure.

FIG. 20 depicts a system 200 for making boron oxide nanoparticles. The system includes a solution comprising boron trioxide 202; and a probe sonicator 204 configured to apply sound energy to the solution to form boron oxide nanoparticles. The solution may comprise a capping agent. The system further comprises a separator 206 configured to isolate the boron oxide nanoparticles by removing the supernatant capping agent. The capping agent may specifically be oleic acid. The system further comprises a lyophilizer 208 configured to vacuum dry the solution. The system further comprises a temperature control system 210 configured to cool the solution during sonication. For instance, an ice bath may be used to regulate the temperature of the solution.

The resulting nanoparticles of the systems, methods, and compositions described herein may have a generally small, uniform construction. For instance, the plurality of nanoparticles may have an average cross-sectional diameter of less than about 100, about 50, about 20, about 10, about 8, about 7, about 6, about 5, or about 4 nanometers. The plurality of nanoparticles may have an average cross-sectional diameter between about 4 and 5 nanometers. The plurality of nanoparticles may have a size and shape that allow the nanoparticles to cross the blood-brain barrier. The particle diameter that is averaged may refer to either the largest cross-sectional diameter or an average cross-sectional diameter for each individual particle. The formed particles may have a generally uniform shape and size. For instance, the plurality of particles may have a cross-sectional diameter standard deviation of less than about 5, about 4, about 3, about 2, about 1, or about 0.5 nanometers. The systems, methods, and compositions described herein may be substantially free of particles above about 100, about 50, about 30, about 20, or about 10 nanometers.

The formed nanoparticles may have a substantially spherical shape. The nanoparticles may comprise boron trioxide and a capping agent. The nanoparticles may consist essentially of boron trioxide and a capping agent. The nanoparticles may consist of boron trioxide and a capping agent. The capping agent may be oleic acid or carboxymethyl-dextran. The boron oxide may be isotopically labeled with Boron-10. The degree of isotope labeling may be sufficient to properly function as an agent for boron neutron capture therapy. The degree of isotope labeling may be higher than the natural occurrence of Boron-10 in nature. For instance, a majority of the Boron atoms in the nanoparticles may be the Boron-10 isotope. Similarly, the boron oxide may alternatively be isotopically labeled with Boron-11. The degree of isotope labeling may be higher than the natural occurrence of Boron-11 in nature. For instance, above 90% of the Boron atoms in the nanoparticles may be the Boron-11 isotope.

Although boron trioxide is often discussed as the starting material in the systems and methods for making boron oxide nanoparticles discussed herein, alternative bulk starting materials may be used, such as boron oxides other than boron trioxide or even alternative boron starting materials. For instance, the bulk starting material may be boric acid, or a similar derivative. Although oleic acid is often discussed as the initial capping agent, alternative capping agents can be used in the solution prior to sonication. The capping agent may be selected to have similar advantageous properties to those of oleic acid, such as a high boiling point or a biocompatibility. Furthermore, as an alternative to applying a sonochemical treatment, microwave radiation may be applied to the solution comprising a boron oxide in the systems and methods described herein.

EXAMPLES

The following examples are provided in order to demonstrate and further illustrate certain embodiments and aspects of the present disclosure and are not to be construed as limiting the scope of the disclosure.

Example 1

An experiment was conducted to validate the sonochemical methods discussed herein. Among other results, the multifaceted experiment allowed for the preparation of uniform, ultra-small (4-5 nm) $B_2O_3$ nanoparticles utilizing bulk $B_2O_3$ powder as the starting material.

The study was commenced by performing a sonochemical treatment on bulk $B_2O_3$ powder (FIG. 2A) in the presence of oleic acid, serving a dual role as the reaction medium and capping agent. Oleic acid was chosen due to its biocompatibility, high boiling point, and widespread use in stabilizing nanoparticles. Without being bound by theory, it is thought that the $B_2O_3$ nanoparticles formed from this treatment got rapidly capped with oleic acid which limited the reaction domain and prevented nanoparticle aggregation, similar to the surface modification observed in metal oxide nanoparticles. The composition, morphology and surface modification of the oleic acid-capped $B_2O_3$ nanoparticles (OA-$B_2O_3$ NPs) were characterized by transmission electron microscopy (TEM), selected area electron diffraction (SAED), Fourier transform infrared (FTIR) spectroscopy, and X-ray photoelectron spectroscopy (XPS).

To synthesize the nanoparticles, a 0.1 g (1.43 mmol) of boron trioxide powder (>98%, Fisher Scientific) and 10 mL (35 mmol) of oleic acid (99%, Sigma Aldrich) were taken in a 50 mL centrifuge tube. The reaction mixture was then probe sonicated (QSonica Q125 sonicator) at 50 amplitude for 3 hours while placed in an ice bath. Following this, the colloidal product obtained was centrifuged at 10,000 rpm for 10 minutes and the supernatant oleic acid was discarded. The solid product was washed with 5 mL of anhydrous hexane (95%, Sigma Aldrich) and vacuum dried on a lyophilizer to produce a fluffy, white powder. When suspended in deionized water, the nanoproduct formed a colloidal dispersion, indicating the presence of hydrophobicity.

Figure 2A:
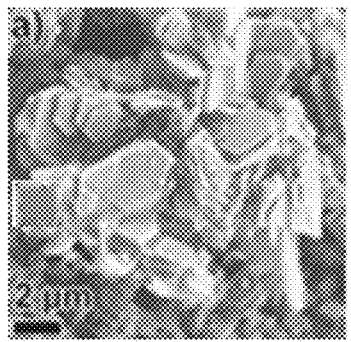
FIGS. 2A-E depict experimental results for the described examples.
Figure 2B:
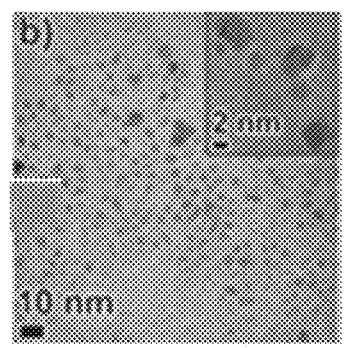
Figure 5:
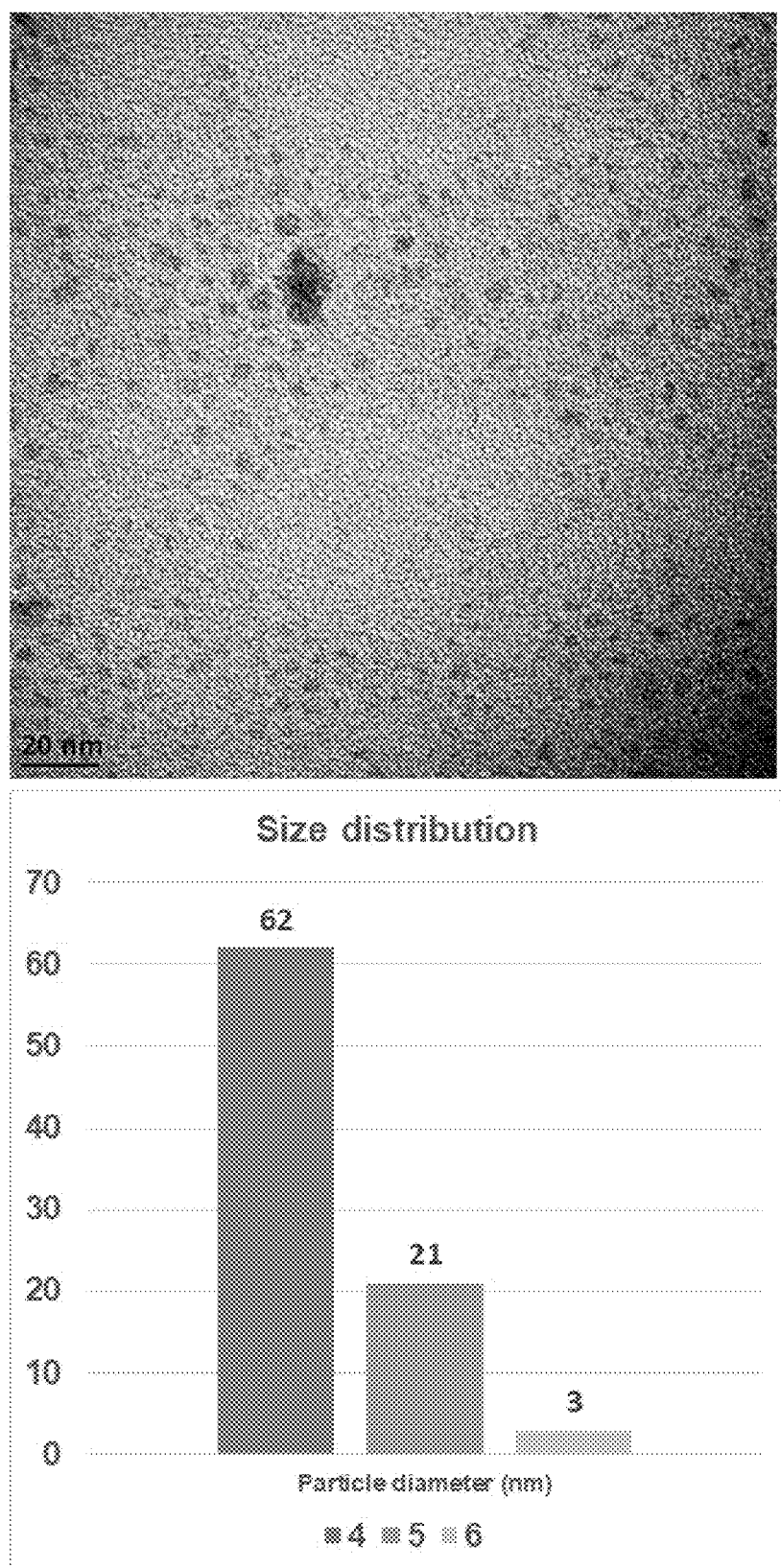
FIG. 5 depicts an experimental TEM image of OA-$B_2O_3$ NPs with size distribution chart. Average particle diameter was calculated to be 4.31±0.54 nm.
Figure 6:
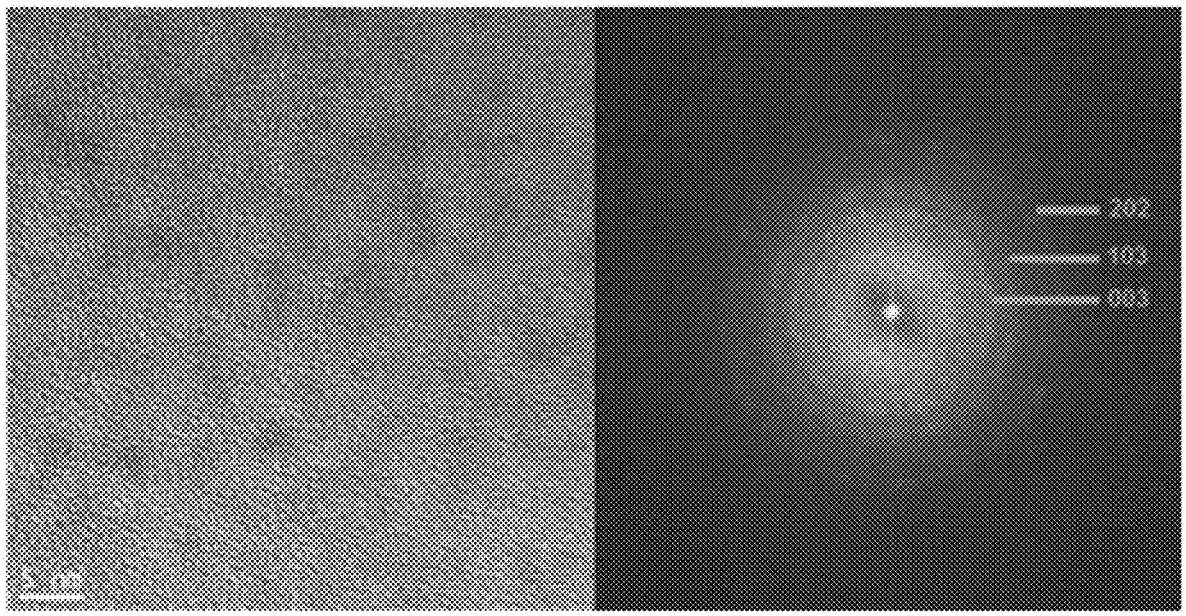
FIG. 6 depicts a HRTEM image of OA-$B_2O_3$ NPs with corresponding live FFT with labeled indices for $B_2O_3$.

Examining the morphology using TEM illustrated that the product from the sonochemical reaction consisted of uniform, spherical, ultra-small nanoparticles with an average size of 4.31±0.54 nm in diameter (FIG. 2B and FIG. 5). This is in stark contrast to the micron-sized platelets comprising the bulk $B_2O_3$ starting material (FIG. 2A). High-resolution TEM coupled with SAED on the nanoparticles showed polycrystalline rings (FIG. 6), which were indexed to $B_2O_3$.

Figure 7:
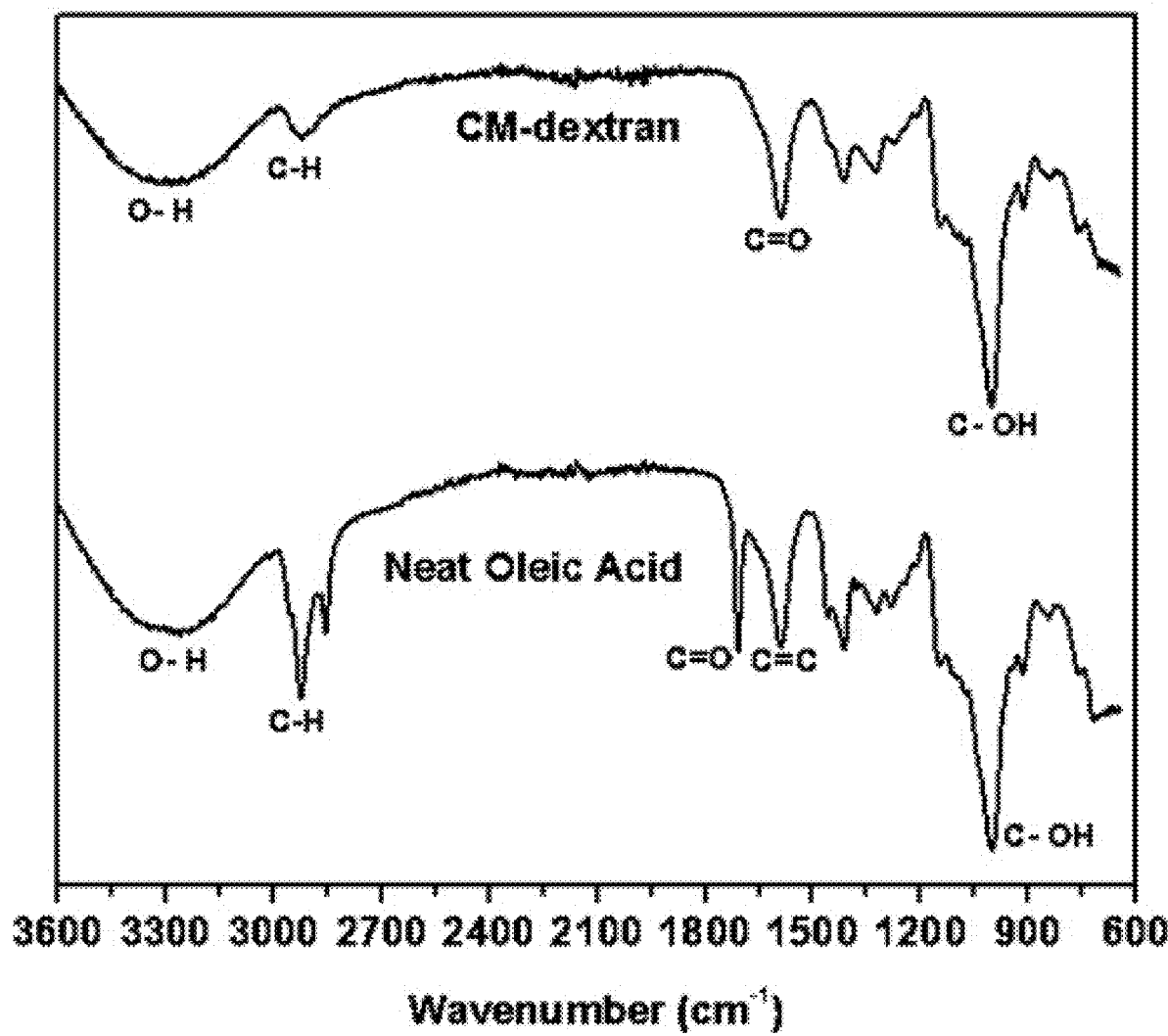
FIG. 7 depicts an experimental FTIR spectra of neat oleic acid (bottom) and pure CM-dextran (top).
Figure 10:
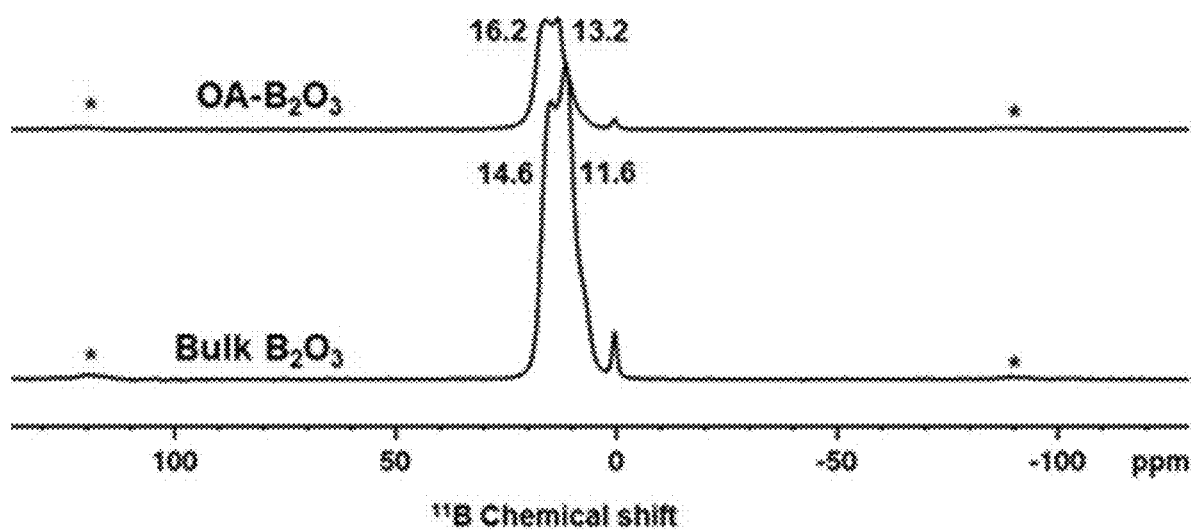
FIG. 10 depicts an experimental $^{11}B$ solid-state MAS NMR spectra of OA-$B_2O_3$ NPs and bulk $B_2O_3$. The upfield 'shoulder peak' observed is likely due to $^{11}B$ having a quadrupolar nucleus.
Figure 11:
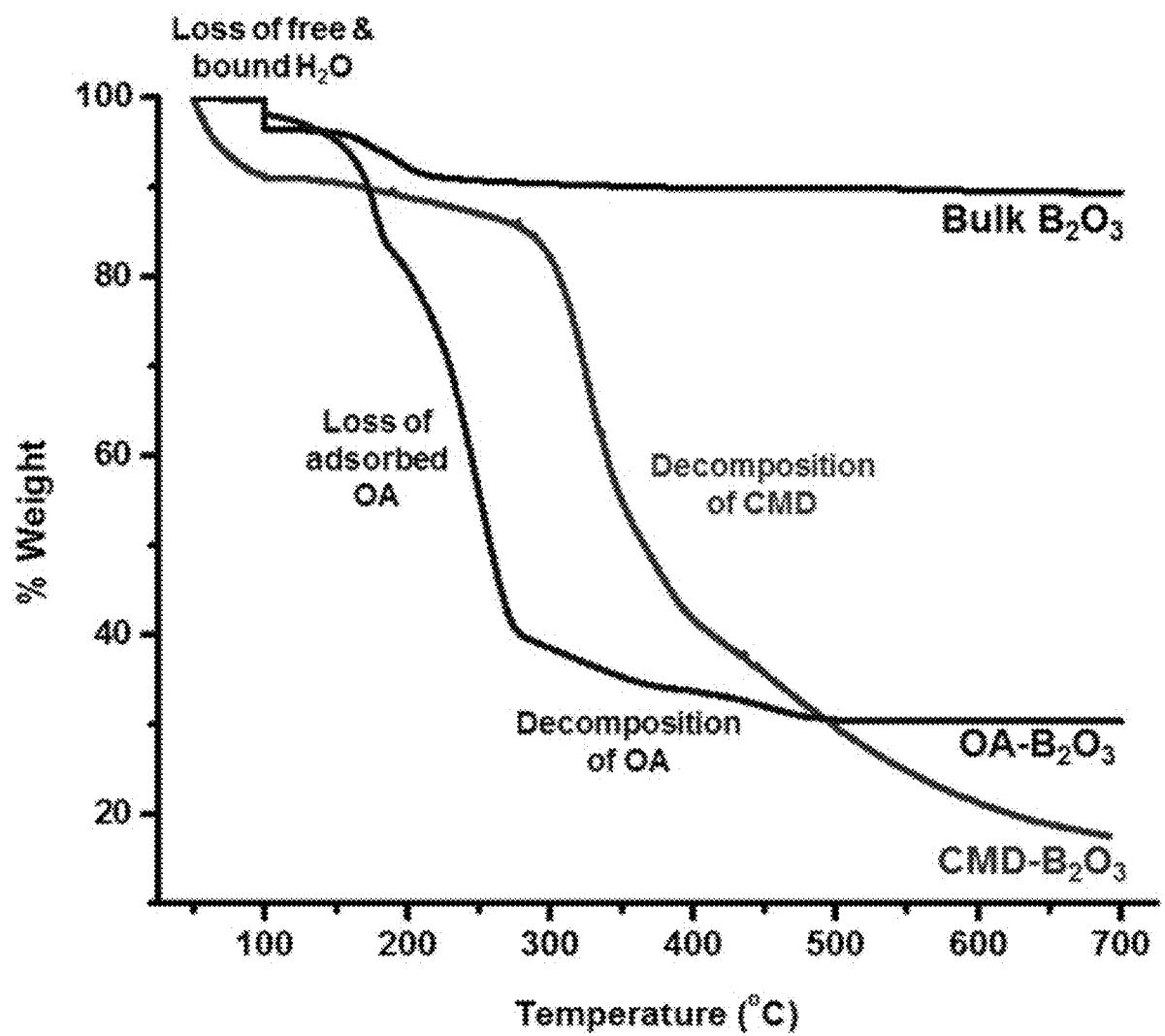
FIG. 11 depicts an experimental TGA curves of bulk $B_2O_3$, OA-$B_2O_3$ NPs and CMD-$B_2O_3$ NPs.

Even though $B_2O_3$ is typically amorphous, it appears that the prolonged heat treatment arising from the high temperature associated with probe sonication led to the formation of crystalline domains in the $B_2O_3$ nanoparticles. The FTIR spectrum of the OA-$B_2O_3$ NPs (FIG. 2D) displayed the typical stretching frequencies of $B_2O_3$ and oleic acid (FIG. 7), confirming the presence of oleic acid on the nanoparticles. We can further utilize the IR stretching frequency values to provide insight on the mechanism of capping on $B_2O_3$ nanoparticles. Upon closer inspection of the $v_{as}$ (COO$^-$) and $v_s$(COO$^-$) IR bands (FIG. 8), we calculated $\Delta v$ to be 247 cm$^{-1}$, which points towards a $\kappa^1$ interaction of oleic acid with the nanoparticle. The surfaces of the bulk $B_2O_3$ and OA-$B_2O_3$ NPs were analyzed by XPS (FIG. 2E). The B 1s peaks (FIG. 2E) shift from 189.5 eV in bare bulk $B_2O_3$ to 188.6 eV in OA-$B_2O_3$ NPs, indicating that the surface B—O environment in OA-$B_2O_3$ NPs has been altered upon capping. The O 1s XPS spectra of OA-$B_2O_3$ NPs (FIG. 2E) also exhibited a binding energy shift to 528.0 eV, compared with 529.4 eV in bulk $B_2O_3$. Further resolution of the O 1s peaks (FIG. 10) indicated the presence of two peaks that are assigned to the B—O and O=C—O binding sites. $^{11}$B solid-state MAS NMR spectroscopy of bulk $B_2O_3$ and OA-$B_2O_3$ NPs revealed a change in chemical shift from 14.6 to 16.2 ppm respectively (FIG. 10). The observed chemical shift of bulk $B_2O_3$ is consistent with crystalline $B_2O_3$, and the downfield shift for OA-$B_2O_3$ NPs can be attributed to deshielding that occurs due to the binding of non-bridging oxygens (COO$^-$ in this case). The zeta potential value of OA-$B_2O_3$ NPs was measured to be −51.3 mV which is indicative of the presence of negatively charged functional groups, such as the carboxylate groups of oleic acid. Moreover, the highly negative zeta potential value shows that the OA-$B_2O_3$ NPs possess good colloidal stability. During our investigations, we also performed control reactions on bulk $B_2O_3$ to determine the optimal conditions for synthesizing ultra-small $B_2O_3$ nanoparticles.

To synthesize oleic acid-capped $B_2O_3$ nanoparticles via microwave treatment, 0.1 g (1.43 mmol) of boron trioxide powder (>98%, Fisher Scientific) and 10 mL (35 mmol) of oleic acid (99%, Sigma Aldrich) were taken in a 22 mL glass tube equipped with Teflon cap. The reaction mixture was then subjected to microwave radiation at 300° C. for 3 hours. Following this, the colloidal product obtained was centrifuged at 10,000 rpm for 10 minutes and the supernatant oleic acid was discarded. The solid product was washed with 5 mL of anhydrous hexane (95%, Sigma Aldrich) and vacuum dried on a lyophilizer to produce a fluffy, white powder.

Figure 12A:
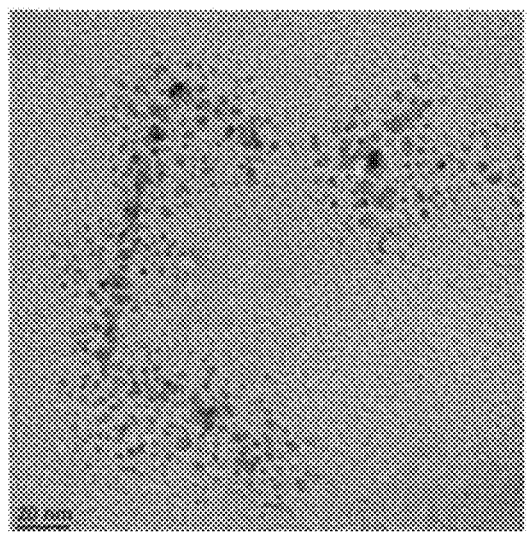
FIGS. 12A-B depict separate experimental low magnification TEM images of $B_2O_3$ nanoparticles obtained from microwave treatment in oleic acid showing a large size distribution ranging from 3 to 40 nm diameter nanoparticles.
Figure 12B:
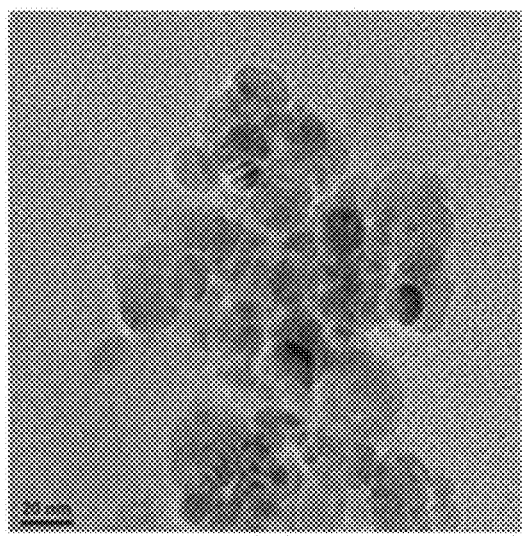
Figure 13A:
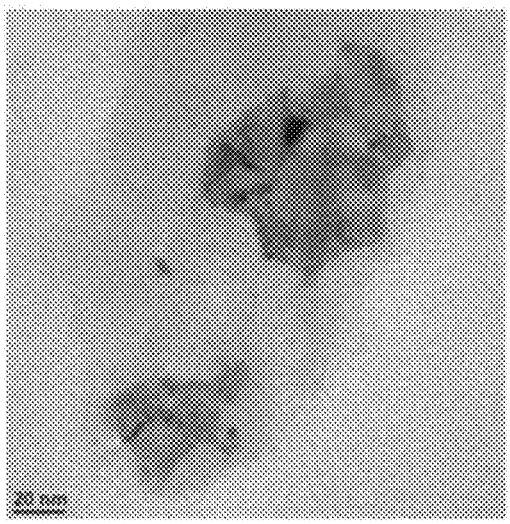
FIGS. 13A-B depict experimental low magnification TEM images of products obtained from the probe sonication reactions of bulk $B_2O_3$ in saturated solution of dextran (4000 MW) (FIG. 13A) and polyethylene glycol solution (FIG. 13B).
Figure 13B:
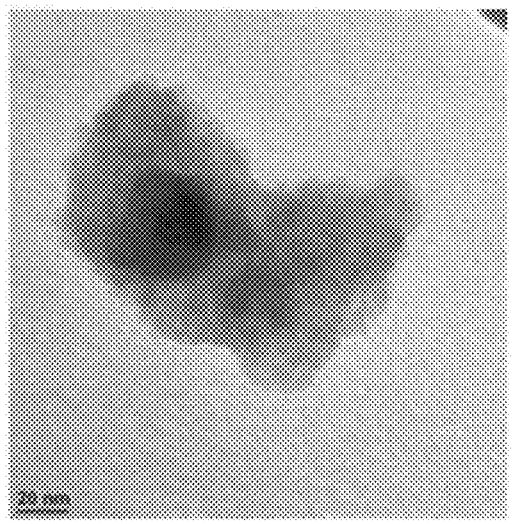

Microwave treatment of bulk $B_2O_3$ in oleic acid yielded $B_2O_3$ nanoparticles with a broad size distribution (FIGS. 12A-B) whereas probe sonication reactions of $B_2O_3$ in the presence of other capping agents (dextran, PEG) produced large fragments that lacked a well-defined morphology (FIGS. 13A-B). Thereby, we established that the combination of probe sonication with oleic acid as the capping agent is most effective for making uniform, ultra-small $B_2O_3$ nanoparticles, of the methods tested.

Figure 3:
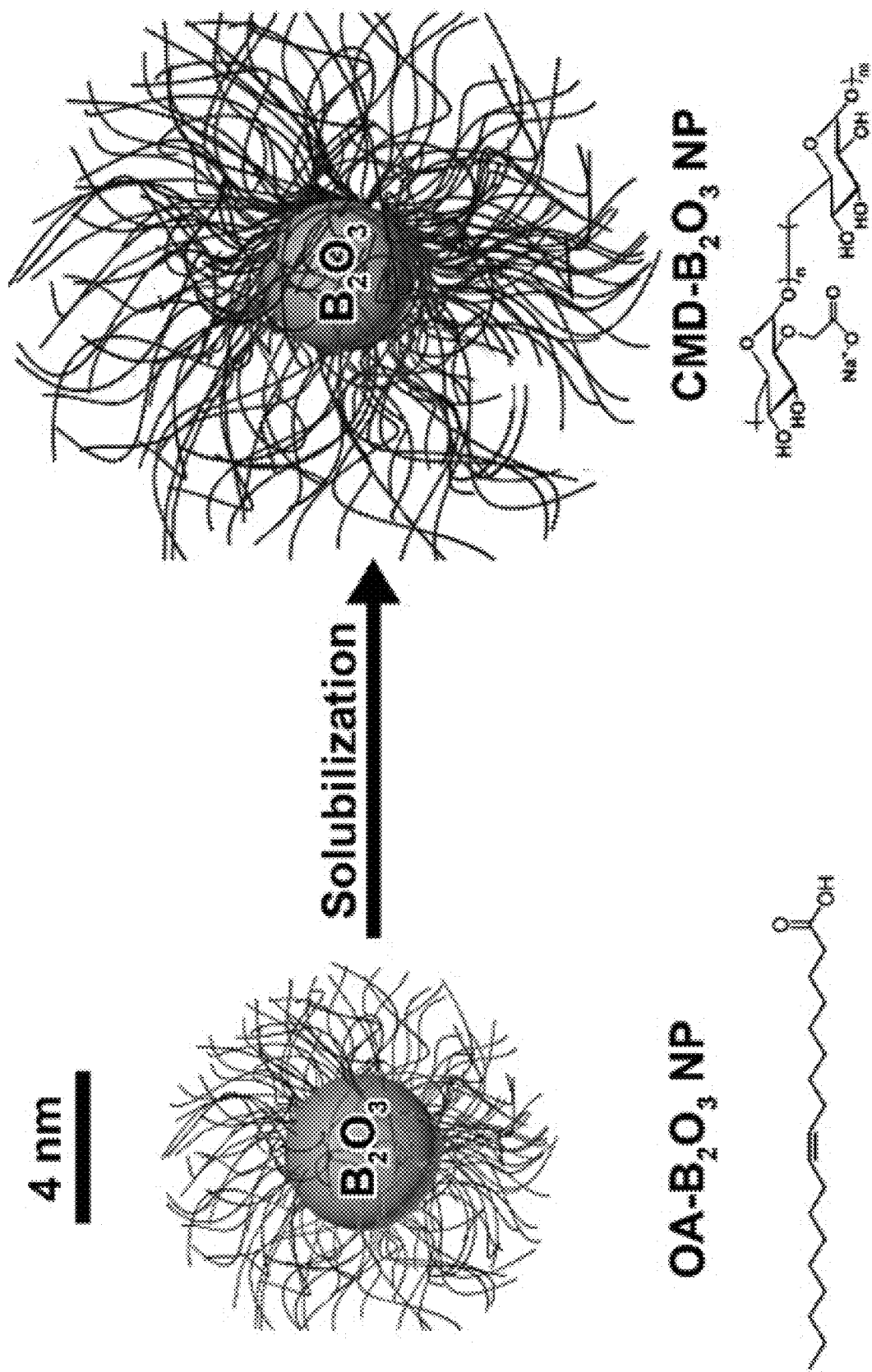
FIG. 3 depicts representation of the phase transfer capping from an OA-$B_2O_3$ NP to a CMD-$B_2O_3$ NP.

In order to explore processing options for $B_2O_3$ NPs, the next step in our synthetic protocol entailed surface modification of the OA-$B_2O_3$ NPs with carboxymethyl-dextran (CMD), a water-soluble capping agent (FIG. 3). This is essential to solubilize the nanoparticles for various aqueous-based applications. We performed a phase transfer reaction on OA-$B_2O_3$ NPs using a saturated solution of CMD and characterized the resulting mixture by various analytical techniques.

To synthesize the carboxymethyl-dextran-capped $B_2O_3$ nanoparticles, 2 mg of the oleic acid-capped $B_2O_3$ nanoparticles were suspended in 1 mL hexane and vigorously stirred in a saturated solution of carboxymethyl-dextran (BioXtra, Sigma Aldrich, 0.015 g in 2 mL deionized water) for 24 hours at 25° C. After stirring, the nanoparticles were centrifuged twice and the supernatant organic layer was discarded. The product was vacuum dried on a lyophilizer to produce a fluffy, white powder. The nanoproduct was fully soluble when suspended in deionized water.

Figure 2C:
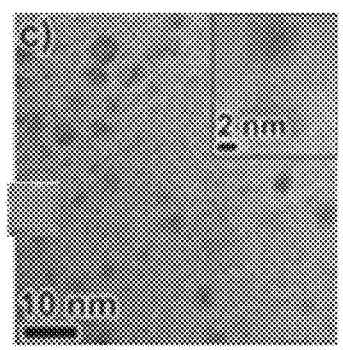
Figure 2D:
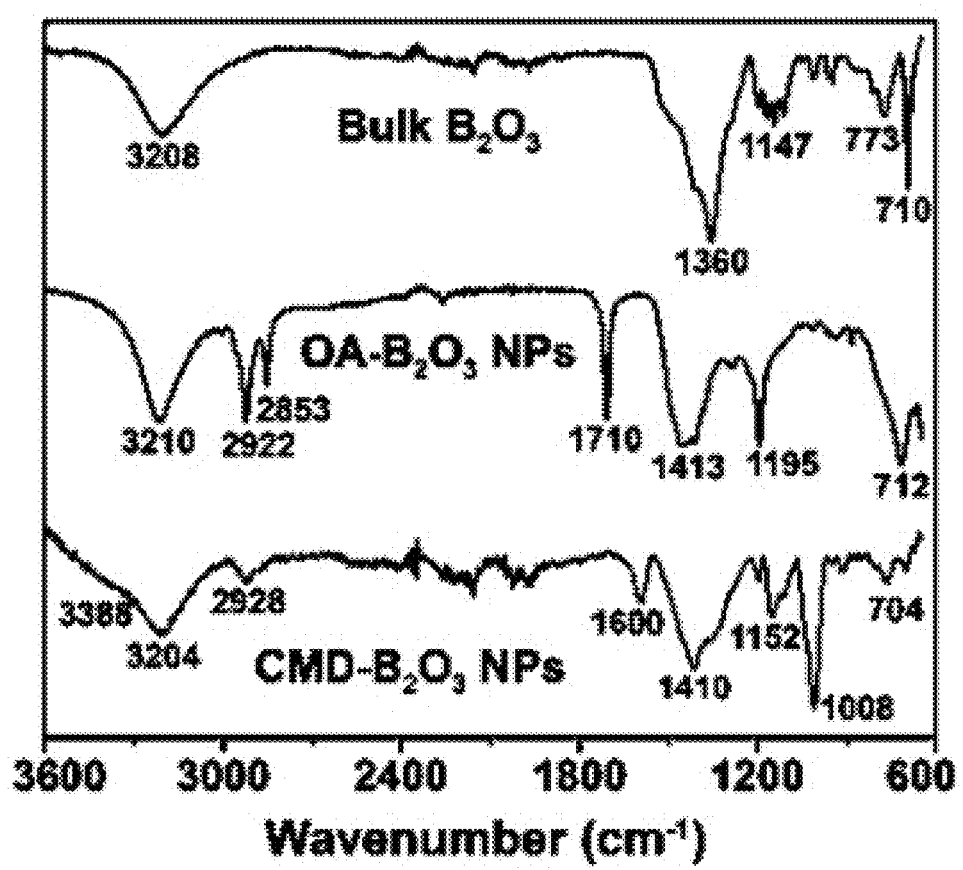
Figure 2E:
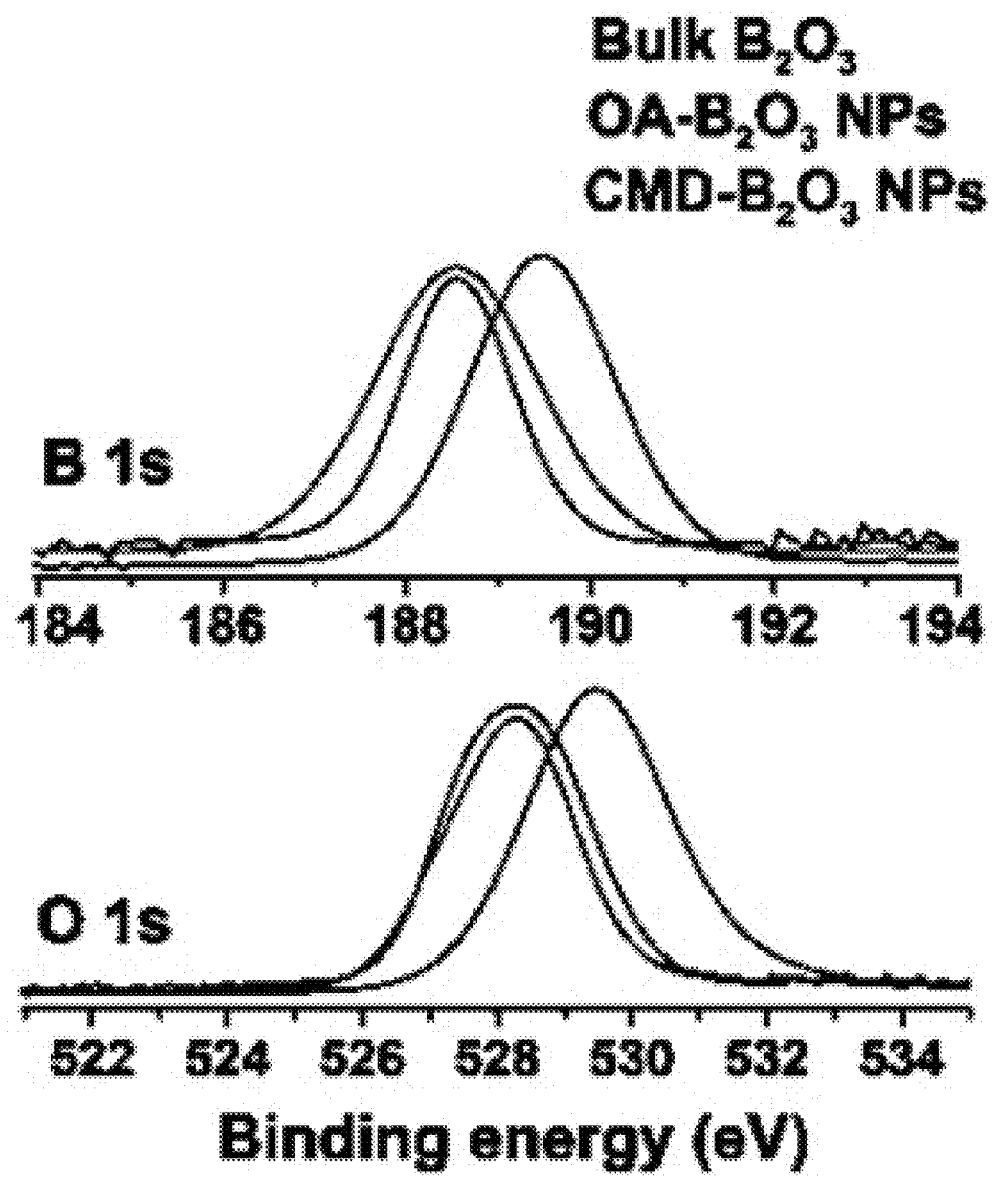
Figure 8:
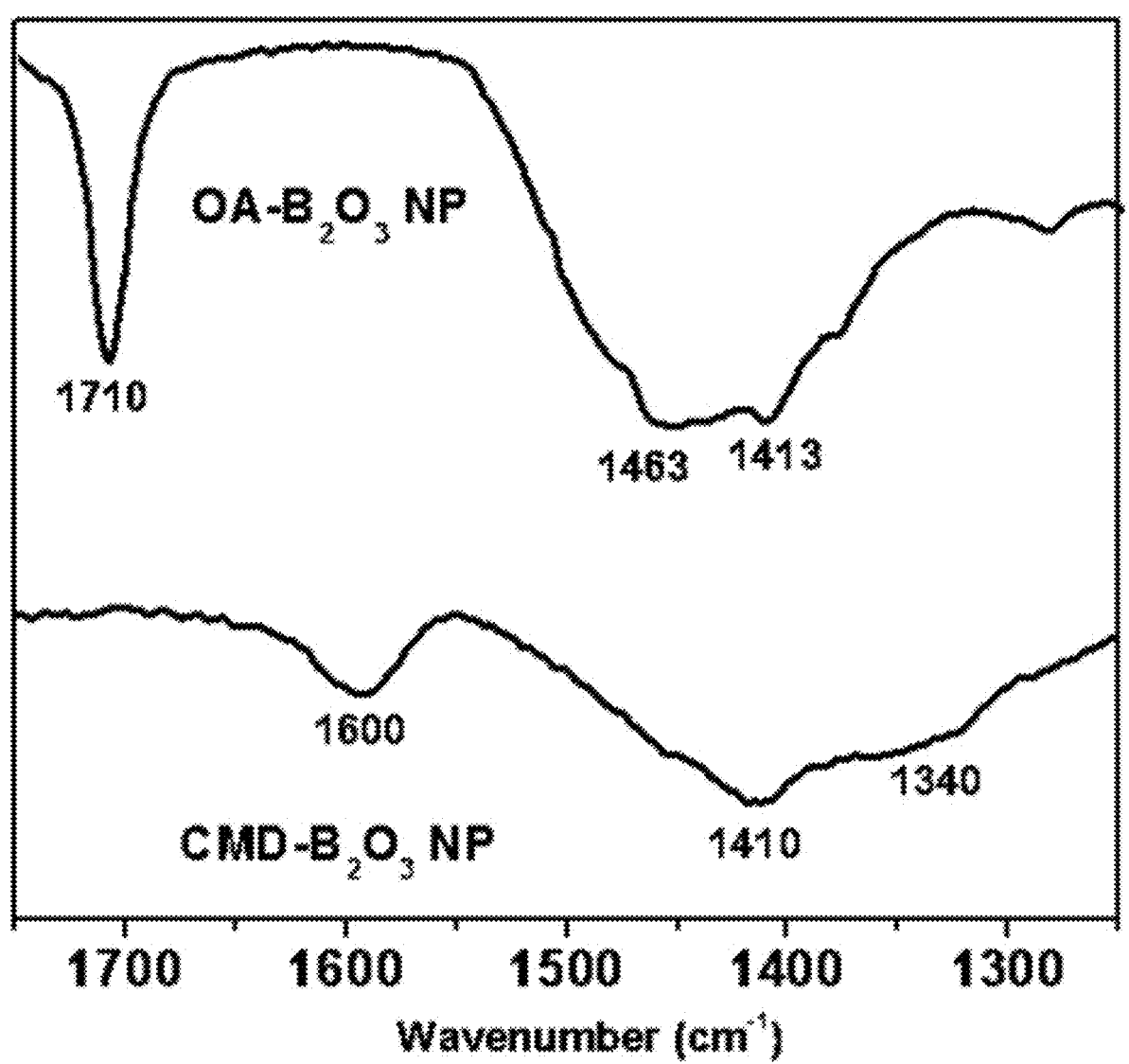
FIG. 8 depicts an experimental FTIR spectra of OA-$B_2O_3$ NPs (top) and CMD-$B_2O_3$ NPs (bottom) illustrating the $v_{as}(COO^-)$ and $v_s(COO^-)$ bands.
Figure 9:
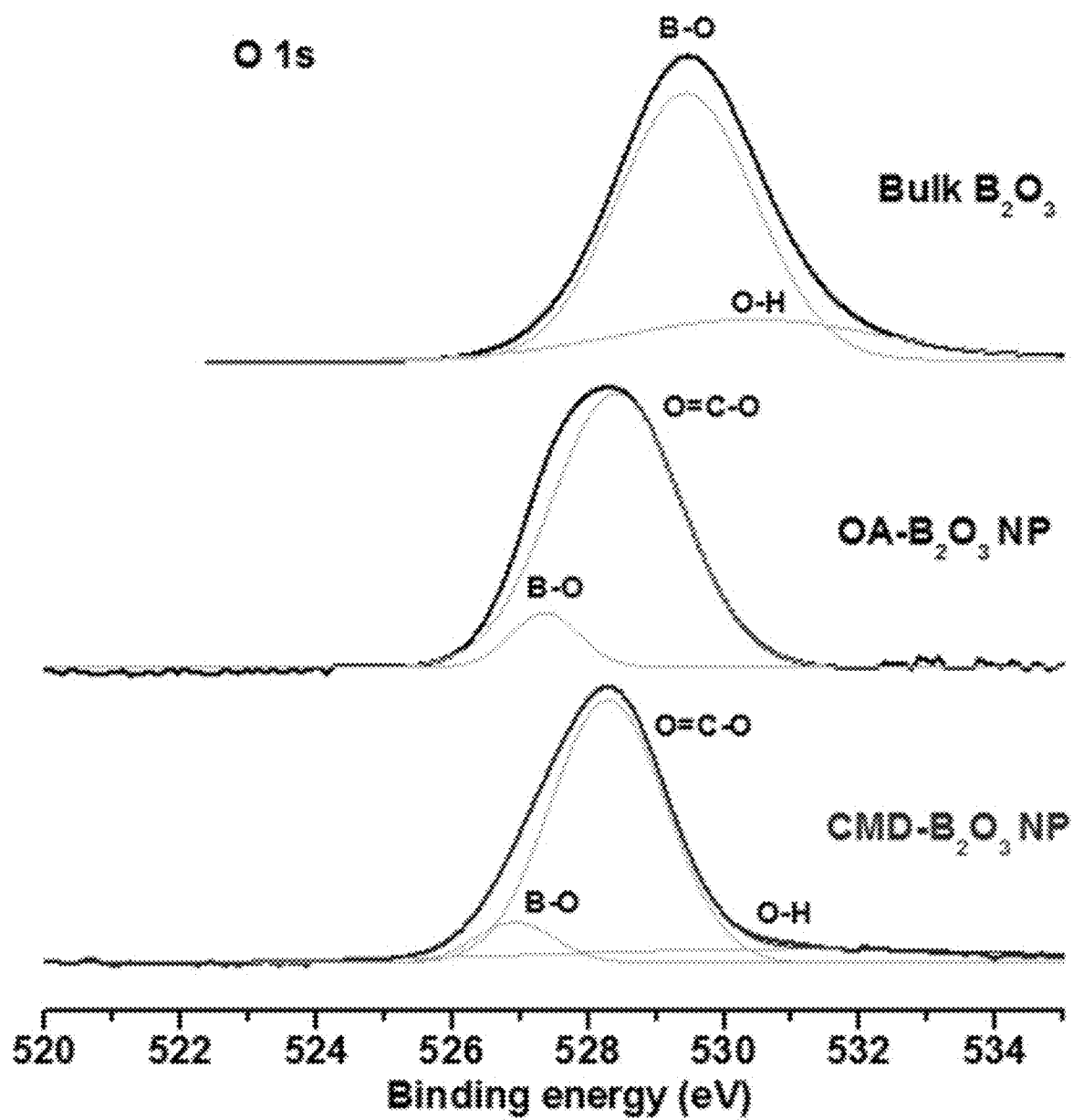
FIG. 9 depicts an experimental O 1s XPS spectra of bulk $B_2O_3$, OA-$B_2O_3$ NPs and CMD-$B_2O_3$ NPs. Lighter lines represent peak-fitted spectra due to multiple O 1s surface environments.

While the resulting NPs became soluble in water, their morphology remained unchanged based on TEM analysis, suggesting successful synthesis of CMD-capped $B_2O_3$ nanoparticles (CMD-$B_2O_3$ NPs, FIG. 2C). Consistent with this hypothesis, the FTIR spectrum of the CMD-$B_2O_3$ NPs (FIG. 2D) displayed stretching frequencies of $B_2O_3$ and carboxymethyl-dextran (FIG. 7), with the $\Delta v$ of 190 $cm^{-1}$ indicating a bridging bidentate capping of the $B_2O_3$ NPs through the carboxylate group (FIG. 8). XPS analyses (FIG. 2E) on CMD-$B_2O_3$ NPs exhibited a B 1s peak at 188.5 eV, comparable to the B—O environment in OA-$B_2O_3$ NPs. The O 1s spectra (FIG. 9) revealed the presence of B—O, O=C—O and O—H sites, signifying a slight change in surface environment occurring as a result of ligand exchange. This trend is close to that observed for OA-$B_2O_3$ NPs, owing to the similarities in the surface binding group of oleic acid and carboxymethyl-dextran. Indeed, the zeta potential of CMD-$B_2O_3$ NPs was measured to be −33.5 mV (Table 6), which is ascribed to the anionic carboxylate groups on the surface. Likewise, the high negative zeta potential value indicates that the CMD-$B_2O_3$ NPs are also stable as colloidal dispersions.

Example 2

Figure 4A:
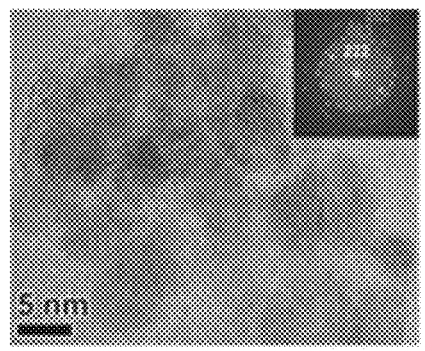
FIGS. 4A-C depict experimental results for the described examples.
Figure 4B:
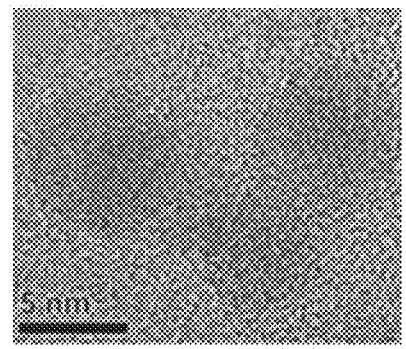
Figure 14:
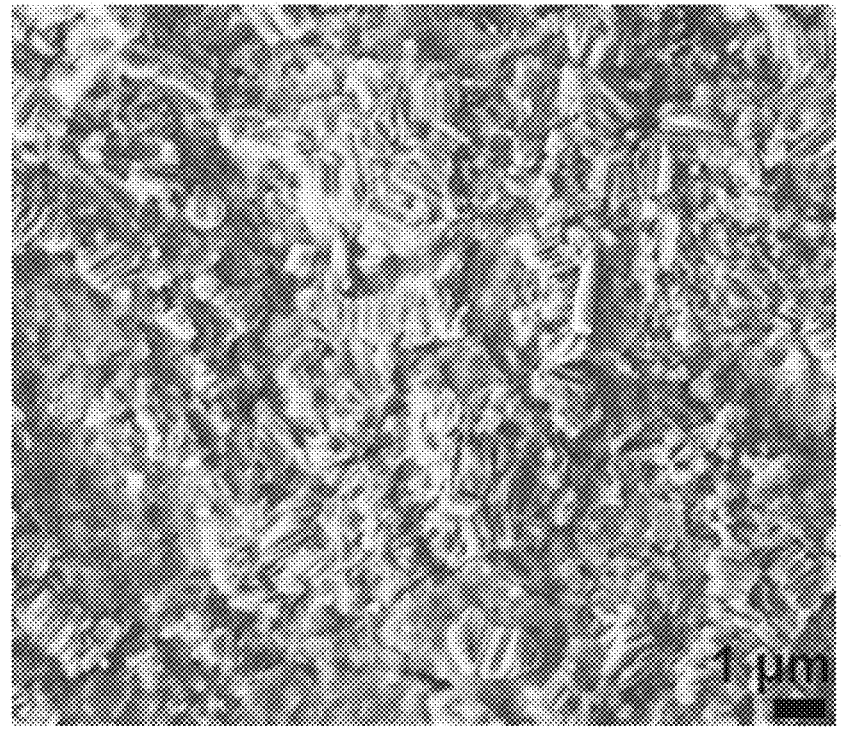
FIG. 14 depicts an experimental SEM image of synthesized bulk $^{10}B_2O_3$ powder.
Figure 15:
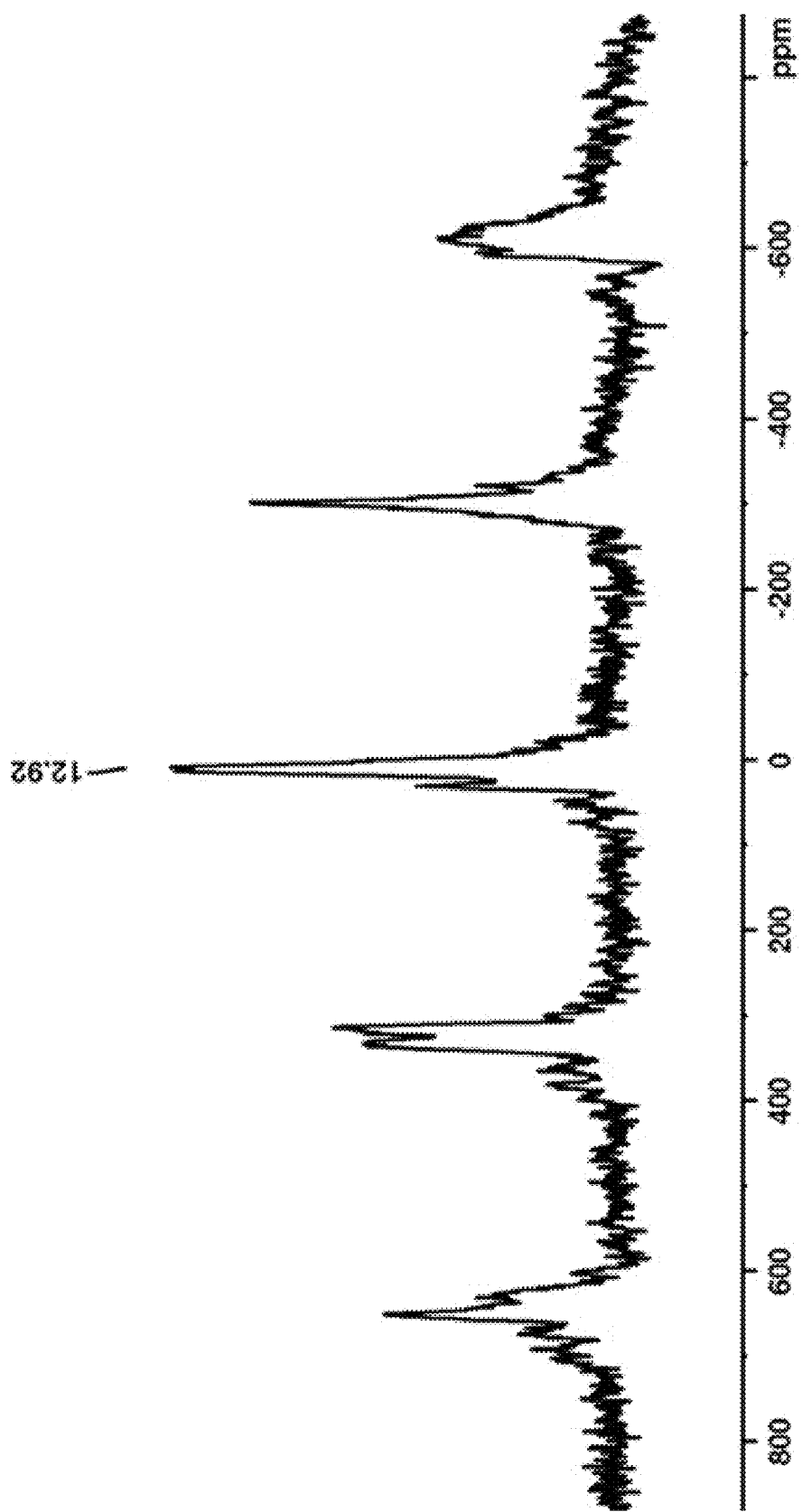
FIG. 15 depicts an experimental $^{10}B$ solid-state MAS NMR spectrum of bulk $^{10}B_2O_3$ powder.
Figure 16:
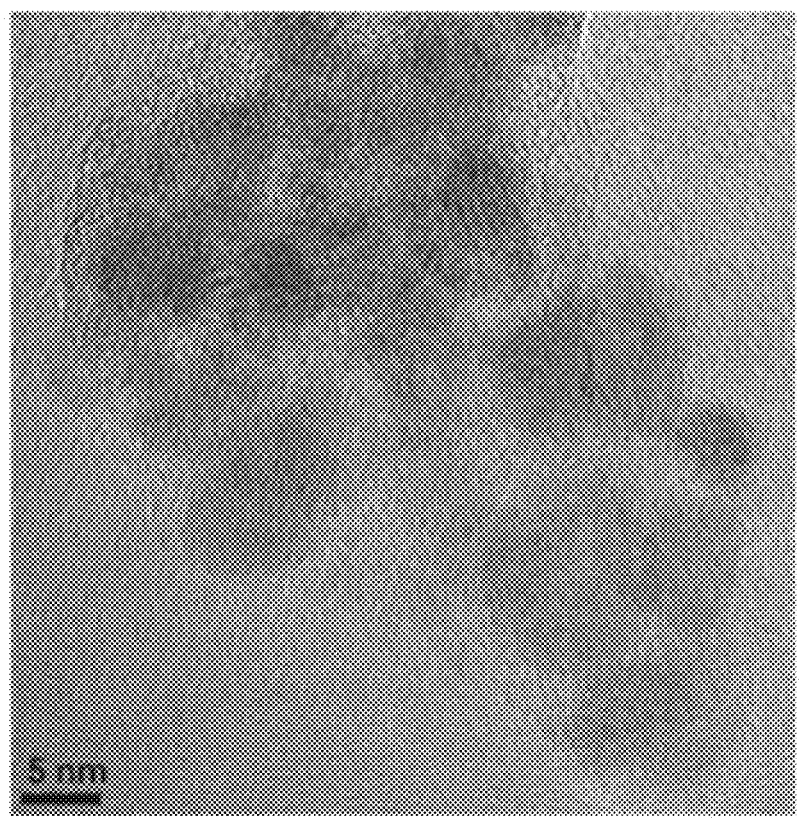
FIG. 16 depicts an experimental TEM image of OA-$^{10}B_2O_3$ NPs with a size distribution chart. Average particle diameter was calculated to be 4.94±0.91 nm.
Figure 16:
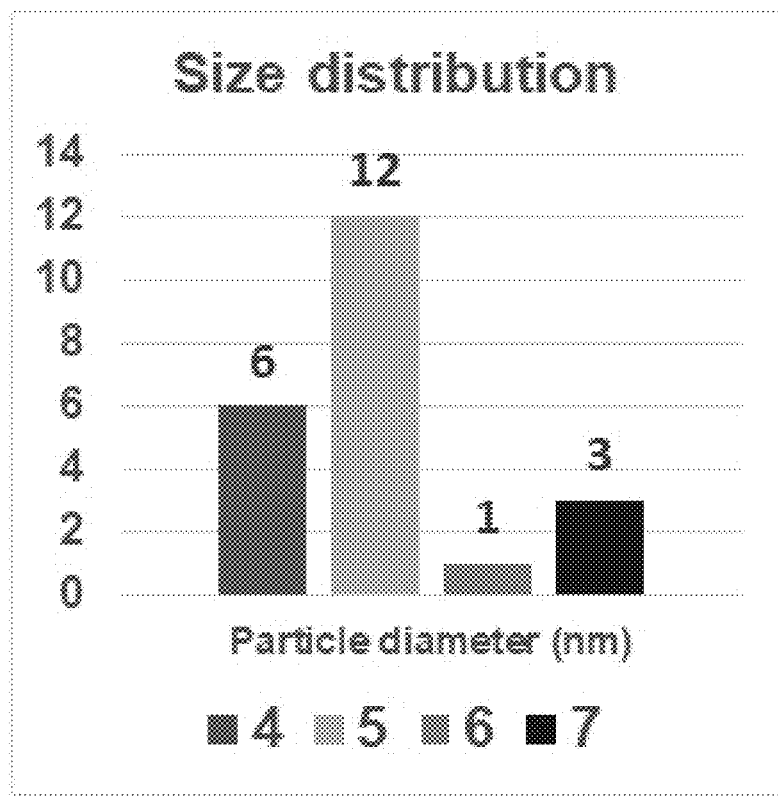
Figure 17:
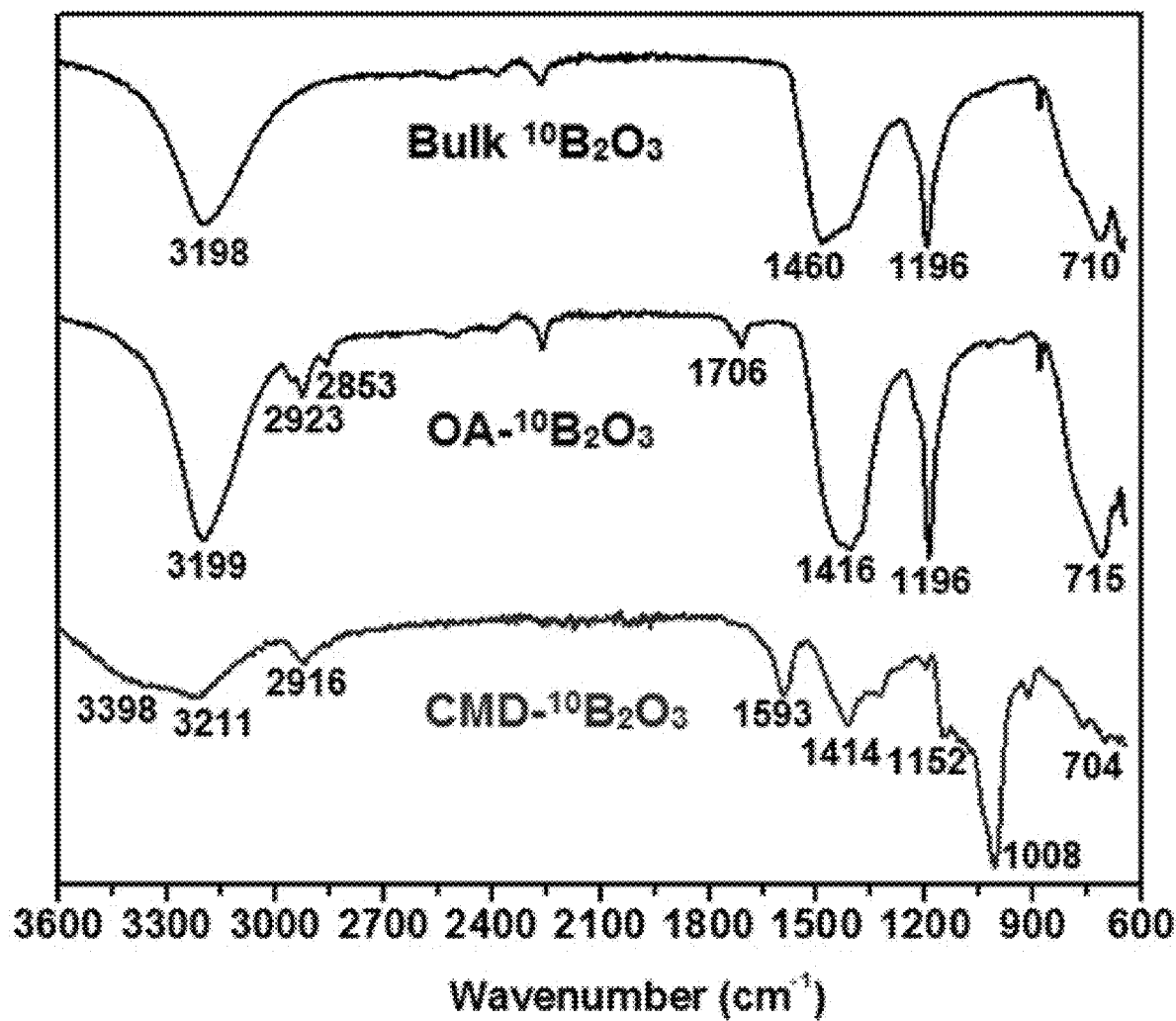
FIG. 17 depicts an experimental ATR-FTIR spectra of bulk $^{10}B_2O_3$, OA-$^{10}B_2O_3$ NPs, and CMD-$^{10}B_2O_3$ NPs.
Figure 18:
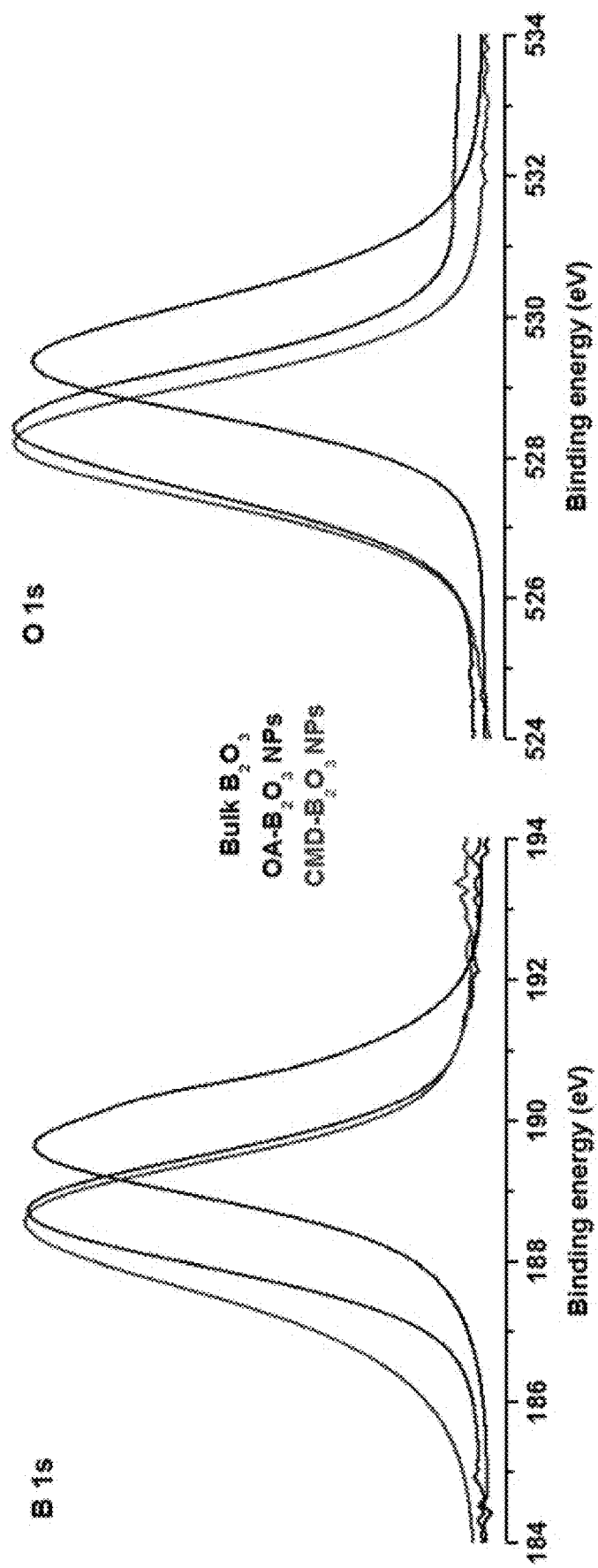
FIG. 18 depicts experimental B 1s and O 1s XPS spectra of bulk $^{10}B_2O_3$, OA-$^{10}B_2O_3$ NPs, and CMD-$^{10}B_2O_3$ NPs.

In order to study the possible use of the method for making boron-rich compounds suitable for boron neutron capture therapy, we synthesized bulk isotopically labelled $^{10}B_2O_3$ (FIG. 14) with the aim of extending the above discussed nanostructuring methodologies to the bulk $^{10}B_2O_3$ powder. We successfully obtained products consisting of ultra-small, spherical shaped, OA-$^{10}B_2O_3$ NPs (FIG. 4A), and CMD-$^{10}B_2O_3$ NPs (FIG. 4B) having an average particle diameter of 4.9±0.9 nm (FIG. 16). SAED on the OA-$^{10}B_2O_3$ NPs (FIG. 4A) showed polycrystalline rings that were indexed to a mixture of $B_2O_3$ polymorphs. The FTIR and XPS spectra for the OA-capped and CMD-capped $^{10}B_2O_3$ NPs (FIGS. 17 and 18) were in agreement with the observations for the corresponding $B_2O_3$ nanoparticles (FIGS. 2D-E) and substantiated the respective surface functionalization.

Figure 4C:
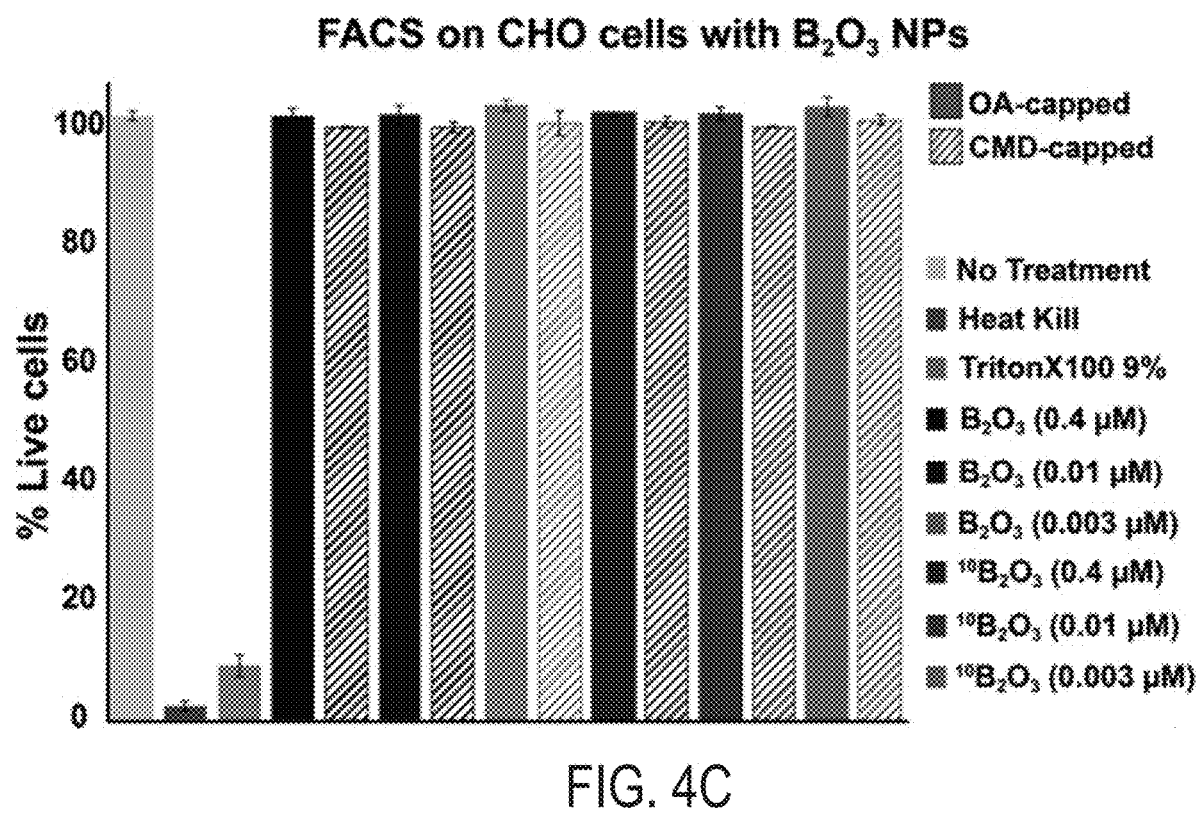
Figure 19:
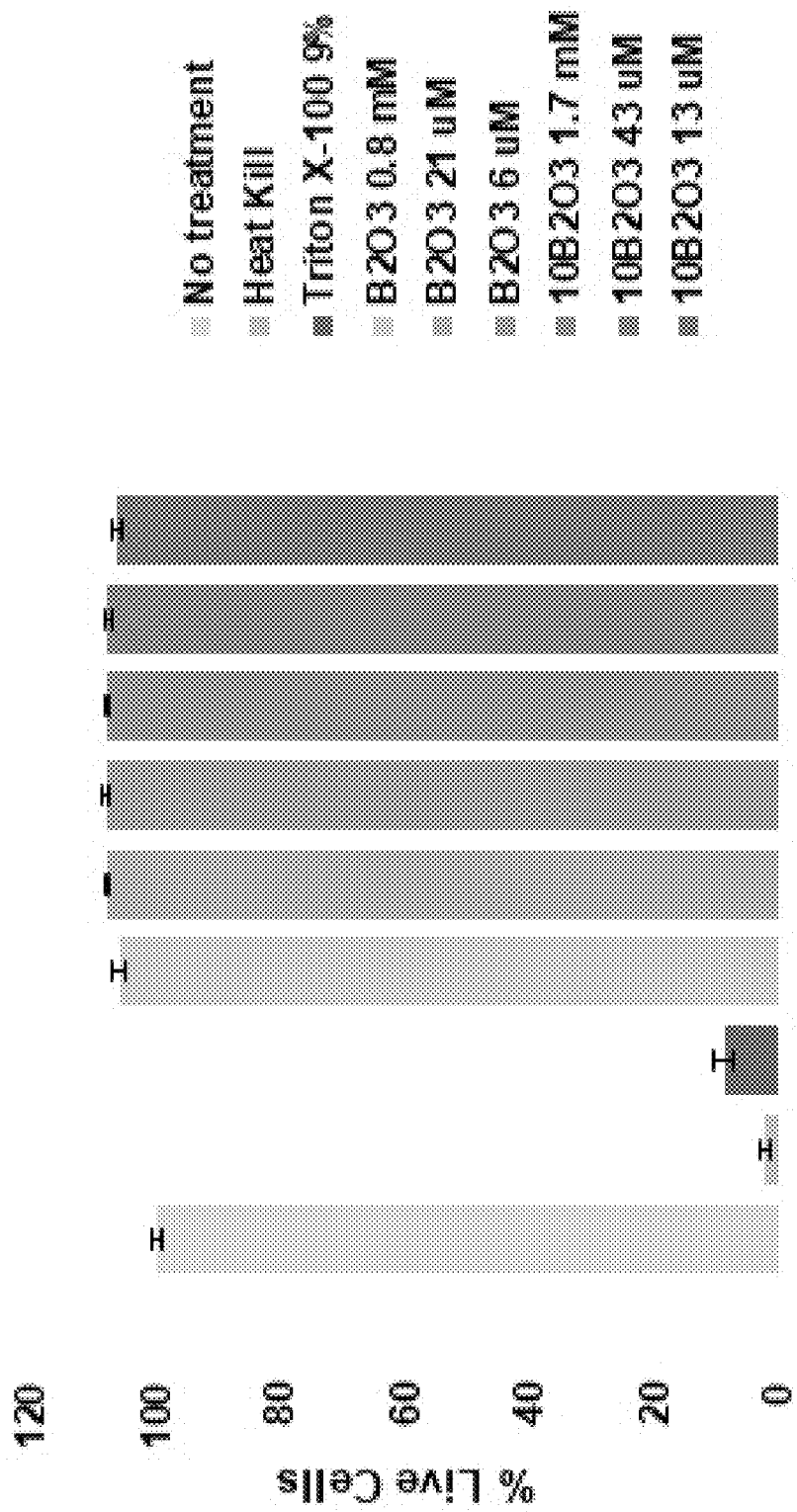
FIG. 19 depicts experimental flow cytometry of high concentration samples of OA-$^{11}B_2O_3$ NPs and OA-$^{10}B_2O_3$ NPs for 24 hours. Dead cells were characterized as exhibiting fluorescence greater than $10^2$. Error bars represent the standard deviation of three replicate samples.

This straightforward two-step synthesis of biocompatible $^{10}B_2O_3$ NPs is especially useful when compared with the multi-step routes currently applied to make molecular $^{10}B$-enriched boron-rich BNCT agents. Particularly, the synthesis of derivitized boron clusters for BNCT proceed through several intermediates, and utilize higher cost $^{10}B_2H_6$ or $^{10}B_3H_8$ as starting materials. In contrast, the above-discussed nanochemistry presents an inexpensive and scalable route towards making $^{10}B$-enriched $B_2O_3$-based BNCT agents from commercially available $^{10}B(OH)_3$ or $^{10}B_2O_3$. In order to investigate the toxicity of the nanoparticles, we employed a flow cytometry assay on Chinese hamster ovarian (CHO) cells in which the cells were incubated with $B_2O_3$ and $^{10}B_2O_3$ nanoparticles for 24 hours, and analyzed via fluorescence activated cell sorting (FACS). Dose-dependent studies showed that the nanoparticles were non-toxic for concentrations ranging from 0.003 µM to 0.4 µm (FIG. 4C). Inductively coupled plasma atomic emission spectroscopy (ICP-AES) was utilized to determine the $B_2O_3$ and $^{10}B_2O_3$ sample concentrations listed in FIG. 4C. Furthermore, we observed that even administering $B_2O_3$ NPs concentrations as high as 1.7 mM proved to be non-toxic to the CHO cells (FIG. 19). The theoretical boron content per $B_2O_3$ nanoparticle of 4 nm diameter was calculated to be ~1500 boron atoms. Therefore, this concentration corresponds to a maximum value of ~6.6×10 boron atoms per cell, which is several orders of magnitude greater than the BNCT required minimum of 1×10$^{11}$ boron atoms. The apparent cell growth observed for cells incubated with OA-$B_2O_3$ NPs and OA-$^{10}B_2O_3$ NPs is consistent with findings that suggest that oleic acid improves cell growth of CHO cells.

The present invention has been described in terms of one or more preferred aspects, and it should be appreciated that many equivalents, alternatives, variations, and modifications, aside from those expressly stated, are possible and within the scope of the invention.

For the avoidance of doubt, aspects of the present disclosure described with respect to the systems and compositions are applicable to the methods and aspects described with respect to the methods are applicable to the systems and compositions. Within this specification embodiments have been described in a way which enables a clear and concise specification to be written, but it is intended and will be appreciated that embodiments may be variously combined or separated without parting from the invention.

Thus, while the invention has been described in connection with particular embodiments and examples, the invention is not necessarily so limited, and that numerous other embodiments, examples, uses, modifications and departures from the embodiments, examples and uses are intended to be encompassed by the claims attached hereto. The entire disclosure of each patent and publication cited herein is incorporated by reference, as if each such patent or publication were individually incorporated by reference herein.

Various features and advantages of the invention are set forth in the following claims.

The invention claimed is:

1. A method of making boron oxide nanoparticles comprising sonochemically treating a reaction mixture comprising a bulk boron oxide and at least one capping agent to form boron oxide nanoparticles.

2. The method of claim 1, wherein the at least one capping agent is oleic acid.

3. The method of claim 2, wherein solubilizing the boron oxide nanoparticles comprises contacting the nanoparticles with a water-soluble capping agent.

4. The method of claim 3, wherein the water-soluble capping agent is carboxymethyl-dextran.

5. The method of claim 1 further comprising isolating and vacuum drying the boron oxide nanoparticles.

6. The method of claim 5, wherein the boron oxide nanoparticles are in the form of a solid powder.

7. The method of claim 1, wherein the boron oxide is boron trioxide.

8. The method of claim 1, wherein the formed nanoparticles have an average cross-sectional diameter of less than 10 nanometers.

9. The method of claim 1 further comprising solubilizing the boron oxide nanoparticles.

10. The method of claim 1, wherein the boron oxide is isotopically labeled with Boron-10 or Boron-11.

* * * * *